United States Patent [19]
Dow

[11] Patent Number: 5,977,124
[45] Date of Patent: Nov. 2, 1999

[54] β-ADRENERGIC AGONISTS

[75] Inventor: Robert L. Dow, Waterford, Conn.

[73] Assignee: Pfizer Inc., New York, N.Y.

[21] Appl. No.: 08/945,551

[22] PCT Filed: May 10, 1995

[86] PCT No.: PCT/IB95/00344

§ 371 Date: Nov. 4, 1997

§ 102(e) Date: Nov. 4, 1997

[87] PCT Pub. No.: WO96/35671

PCT Pub. Date: Nov. 14, 1996

[51] Int. Cl.[6] ................. C07D 213/73; C07D 239/42; A61K 31/44

[52] U.S. Cl. ............. 514/272; 514/352; 544/332; 546/312; 548/110; 548/252; 548/253; 556/416

[58] Field of Search .............. 544/332; 546/312; 548/110, 252, 253; 556/416; 514/272, 352

[56] References Cited

U.S. PATENT DOCUMENTS

| | | | |
|---|---|---|---|
| 4,358,455 | 11/1982 | Atkinson et al. | 424/263 |
| 4,800,206 | 1/1989 | Alig et al. | 514/322 |
| 4,988,714 | 1/1991 | Alig et al. | 514/357 |
| 5,019,578 | 5/1991 | Fisher et al. | 514/275 |
| 5,216,170 | 6/1993 | Lindel et al. | 514/322 |
| 5,599,966 | 2/1997 | Bron et al. | 514/322 |

FOREIGN PATENT DOCUMENTS

| | | |
|---|---|---|
| 0105053 | 4/1984 | European Pat. Off. |
| 0254856 | 6/1987 | European Pat. Off. |
| 0278728 | 8/1988 | European Pat. Off. |
| 0318092 | 5/1989 | European Pat. Off. |
| 0611003 | 8/1994 | European Pat. Off. |
| 8165276 | 6/1996 | Japan . |
| 751969 | 3/1975 | South Africa . |
| 9322277 | 11/1993 | WIPO . |
| 9414775 | 7/1994 | WIPO . |
| 9425427 | 11/1994 | WIPO . |
| 9429290 | 12/1994 | WIPO . |

OTHER PUBLICATIONS

A. R. Peters; Veterninary Record; 124; 417–420 (1989).
English Translation of JP 8–165276, 1996.
English language Abstracts (2) of Japanese 8165276 plus page of formulae.

*Primary Examiner*—Zinna Northington Davis
*Attorney, Agent, or Firm*—Peter C. Richardson; Gregg C. Benson; James T. Jones

[57] ABSTRACT

(I)

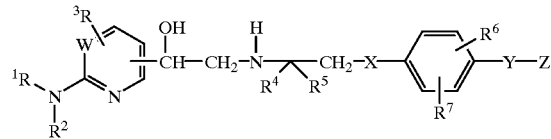

β-adrenergic agonists for the treatment of diseases/conditions such as obesity and diabetes. The compounds have formula (I), wherein $R^1, R^2, R^3, R^4, R^5, R^6, R^7$, W, X, Y and Z are as defined in the specification.

21 Claims, No Drawings

β-ADRENERGIC AGONISTS

This is a National Phase filing under 35 U.S.C. §371 based on PCT/IB95/00344 which was filed internationally on May 10, 1995.

BACKGROUND OF THE INVENTION

The present invention relates to certain compounds of the formula (I) depicted below, which are β-adrenergic receptor agonists and accordingly have utility as, inter alia, hypoglycemic and antiobesity agents. The invention also relates to methods for the compounds use and to pharmaceutical compositions containing them. The compounds of the present invention also possess utility for increasing lean meat deposition and/or improving the lean meat to fat ratio in edible animals, i.e. ungulate animals and poultry.

The compounds of this invention further possess utility in the treatment of intestinal motility disorders, depression, prostate disease, dyslipidemia, and airway inflamatory disorders such as asthma and obstructive lung disease.

The disease diabetes mellitus is characterized by metabolic defects in production and utilization of carbohydrates which result in the failure to maintain appropriate blood sugar levels. The result of these defects is elevated blood glucose or hyperglycemia. Research in the treatment of diabetes has centered on attempts to normalize fasting and postprandial blood glucose levels. Current treatments include administration of exogenous insulin, oral administration of drugs and dietary therapies.

Two major forms of diabetes mellitus are recognized. Type I diabetes, or insulin-dependent diabetes, is the result of an absolute deficiency of insulin, the hormone which regulates carbohydrate utilization. Type II diabetes, or non-insulin dependent diabetes, often occurs with normal, or even elevated levels of insulin and appears to be the result of the inability of tissues to respond appropriately to insulin. Most of the Type II diabetics are also obese.

The compounds of the present invention and the pharmaceutically active salts thereof effectively lower blood glucose levels when administered orally to mammals with hyperglycemia or diabetes.

The compounds of the present invention also reduce body weight or decrease weight gain when administered to mammals. The ability of these compounds to affect weight gain is due to activation of β-adrenergic receptors which stimulate the metabolism of adipose tissue.

β-Adrenergic receptors have been categorized into $β_1$, $β_2$ and $β_3$-subtypes. Agonists of β-receptors promote the activation of adenyl cyclase. Activation of $β_1$-receptor receptors invokes increases in heart rate while activation of $β_2$-receptors induces relaxation of skeletal muscle tissue which produces a drop in blood pressure and the onset of smooth muscle tremors. Activation of $β_3$-receptors is known to stimulate lipolysis (the breakdown of adipose tissue triglycerides to glycerol and free fatty acids) and metabolic rate (energy expenditure), and thereby promote the loss of fat mass. Compounds that stimulate β-receptors are therefore useful as anti-obesity agents, and can also be used to increase the content of lean meat in edible animals. In addition, compounds which are $β_3$-receptor agonists have hypoglycemic or anti-diabetic activity, but the mechanism of this effect is unknown.

Until recently $β_3$-adrenergic receptors were thought to be found predominantly in adipose tissue. $β_3$-receptors are now known to be located in such diverse tissues as the intestine (*J. Clin. Invest.*, 91, 344 (1993)) and the brain (*Eur. J. Pharm.*, 219,193 (1992)). Stimulation of the $β_3$-receptor has been demonstrated to cause relaxation of smooth muscle in colon, trachea and bronchi. *Life Sciences*, 44(19), 1411 (1989); *Br. J. Pharm.*, 112, 55 (1994); *Br. J. Pharmacol.*, 110, 1311 (1993). For example, stimulation of $β_3$-receptors has been found to induce relaxation of histamine-contracted guinea pig ileum, *J.Pharm.Exp.Ther.*, 260, 1, 192 (1992).

The $β_3$-receptor is also expressed in human prostate. Because stimulation of the $β_3$-receptor causes relaxation of smooth muscles that have been shown to express the $β_3$-receptor (e.g. intestine), one skilled in the art would predict relaxation of prostate smooth muscle. Therefore $β_3$-agonists will be useful for the treatment or prevention of prostate disease.

European Patent publication 516,349, published Dec. 2, 1992, refers to certain 2-hydroxyphenethyl amines which possess antiobesity, hypoglycemic and related utilities.

U.S. Pat. No. 4,358,455 is concerned with certain heterocyclic compounds of the formula Het-CHOH-$CH_2$-NH-aralkyl, useful for treating glaucoma and cardiovascular disorders.

U.S. Pat. No. 5,030,640 concerns certain α-heterocyclic ethanol amino alkyl indoles, useful as growth promoters, bronchodilators, antidepressants and antiobesity agents.

U.S. Pat. No. 5,019,578 concerns certain α-heterocyclic ethanol amines useful as growth promoters.

SUMMARY OF THE INVENTION

This invention relates to compounds having the formula I

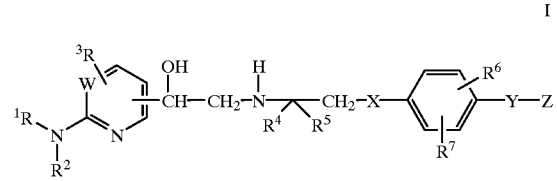

wherein:
  $R^1$, $R^2$, $R^4$ and $R^5$ are independently hydrogen or ($C_1$–$C_6$) alkyl;
  $R^3$, $R^6$ and $R^7$ are independently hydrogen, halogen, ($C_1$–$C_6$)alkyl, nitro, cyano, trifluoromethyl, $SO_2R^8$, $SO_2NR^9R^{10}$, $NR^9R^{10}$, $COR^{11}$, $CO_2R^9$, ($C_1$–$C_6$)alkoxy, $NR^9SO_2R^8$, $NR^9COR^{11}$, $NR^9CO_2R^9$ or $OR^9$;
  $R^8$ is independently ($C_1$–$C_6$)alkyl or ($C_1$–$C_6$)alkoxy($C_1$–$C_6$)alkyl;
  $R^9$ and $R^{10}$ are independently hydrogen, ($C_1$–$C_6$)alkyl, ($C_3$–$C_8$)cycloalkyl, or ($C_1$–$C_6$)alkoxy($C_1$–$C_6$)alkyl;
  $R^{11}$ is independently hydrogen, ($C_1$–$C_6$)alkyl, $NR^9R^{10}$, ($C_3$–$C_8$)cycloalkyl, or ($C_1$–$C_6$)alkoxy($C_1$–$C_6$)alkyl wherein $R^9$ and $R^{10}$ are as defined above;
  W is N, CH, or when $R^3$ is bonded to W, $CR^3$ wherein $R^3$ can be any of the values listed above for $R^3$ in addition to H;

X and Y are independently a direct link (i.e. a covalent bond), oxygen, sulfur, or $NR^1$ wherein $R^1$ is as defined above;

Z is $(CH_2)_m OR^9$, $(CH_2)_n CO_2H$, $(CH_2)_n COR^{11}$, $(CH_2)_n SO_2 NR^9 R^{10}$, $(CH_2)_n-NR^9 SO_2 R^8$, $(CH_2)_n P(O)(OR^1)(OR^2)$, $(CH_2)_n-O-(CH_2)_m CO_2H$, $(CH_2)_n-O-(CH_2)_m COR^{11}$, $(CH_2)_n-O-(CH_2)_m P(O)(OR^1)(OR^2)$, $(CH_2)_n-O-(CH_2)_m SO_2 NR^9 R^{10}$, or $(CH_2)_n-O-(CH_2)_m-NR^9 SO_2 R^8$ wherein $R^1$, $R^2$, $R^8$, $R^9$, $R^{10}$ and $R^{11}$ are as defined above;

m is 1 to 6;

n is 0 to 6, provided that if Y is O or S, n is not 0;

pharmaceutically acceptable prodrugs of said compounds; and pharmaceutically acceptable salts of said compounds and said prodrugs.

Compounds according to the invention are β-adrenergic receptor agonists. In general, those compounds wherein the Y-Z moiety terminates in a free carboxylic acid (COOH) group constitute a preferred subgroup because they are selective agonists for the $β_3$-subtype adrenergic receptor. Selectivity for $β_3$-subtype is desirable since such selectivity reduces or avoids undesirable effects of $β_1$- and/or $β_2$-agonism, such as increased heart rate, smooth muscle tremoring, and decreased blood pressure. This particular group is referred to as "free carboxylic acids" below.

Another preferred subgroup of compounds includes those free carboxylic acids of formula I wherein X is oxygen.

Another preferred subgroup includes those free carboxylic acids of formula I wherein X is oxygen and W is CH.

Another preferred subgroup includes those free carboxylic acids of formula I wherein X is oxygen, W is CH, and each of $R^1$, $R^2$, $R^3$, $R^4$, $R^5$, $R^6$, and $R^7$ is H.

Another preferred subgroup includes those compounds of formula I wherein X is oxygen, W is CH, each of $R^1$, $R^2$, $R^3$, $R^4$, $R^5$, $R^6$, and $R^7$ is H, and Y is oxygen or a direct link.

Specific compounds include the following:

(4-(2-(2-(6-aminopyridin-3-yl)-2(R)-hydroxyethylamino)ethoxy)phenyl)acetic acid;

(4-(2-(2-(6-aminopyridin-3-yl)-2(R)-hydroxyethylamino)ethoxy)phenoxy)acetic acid;

4-(2-(2-(6-aminopyridin-3-yl)-2(R)-hydroxyethylamino)ethoxy)benzoic acid; and (4-(2-(2-(6-aminopyridin-3-yl)-2(R)-hydroxyethylamino)ethoxy)phenyl)propionic acid;

Salt forms of the above compounds are also preferred.

The present invention also relates to a therapeutic composition, useful for treating a condition, disease, or disorder in a mammal, including any of the conditions, diseases and/or disorders disclosed herein, comprising an amount of a compound of formula I, or a prodrug thereof, or a pharmaceutically acceptable salt of said compound or prodrug, effective in treating such condition, disease, or disorder, and a pharmaceutically acceptable carrier. Specific conditions, diseases, and/or disorders which are treatable with such compositions include diabetes, hyperglycemia, obesity, intestinal motility disorders, airway inflammatory disorders, depression, prostate disease, and dyslipidemia.

This invention also relates to a method of treating a condition selected from the group consisting of diabetes, hyperglycemia and obesity in a mammal, comprising administering to a mammal in need of such treatment an amount of a compound of formula I, or a prodrug thereof, or a pharmaceutically acceptable salt of said compound or prodrug, effective in treating such condition.

This invention also relates to a composition, useful for increasing the content of lean meat in edible animals, comprising an amount of a compound of formula I, or a prodrug thereof, or a pharmaceutically acceptable salt of said compound or prodrug, effective in increasing said content, and a pharmaceutically acceptable carrier.

This invention also relates to a method of increasing the content of lean meat in edible animals comprising administering to an edible animal an amount of a compound of formula I, or a prodrug thereof, or a pharmaceutically acceptable salt of said compound or prodrug, effective in increasing said content.

This invention also relates to a method for treating prostate disease in a mammal, preferably a human, comprising administering to a mammal in need of such treatment an amount of a compound of formula I, or a prodrug thereof, or a pharmaceutically acceptable salt of said compound or prodrug, effective in treating such disease.

The present invention also relates to a method of treating a condition selected from the group consisting of intestinal motility disorders such as irritable bowel syndrome, peptic ulceration, esophagitis, gastritis and duodenitis, (including that induced by H. pylori), intestinal ulcerations (including inflammatory bowel disease, ulcerative colitis, Crohn's disease and proctitis) and gastrointestinal ulcerations in a mammal, preferably a human, comprising administering to a mammal in need of such treatment an amount of a compound of formula I, or a prodrug thereof, or a pharmaceutically acceptable salt of said compound or prodrug, effective in treating such condition.

The present invention also relates to a method for treating depression in a mammal, preferably a human, comprising administering to a mammal in need of such treatment an amount of a compound of formula I, or a prodrug thereof, or a pharmaceutically acceptable salt of said compound or prodrug, effective in treating depression.

The present invention also relates to a method for treating dyslipidemia in a mammal, preferably a human, comprising administering to a mammal in need of such treatment an amount of a compound of formula I, or a prodrug thereof, or a pharmaceutically acceptable salt of said compound or prodrug, effective in treating dyslipidemia.

The present invention also relates to a method of treating airway inflamatory disorders, especially asthma, comprising administering to a mammal in need of such treatment an amount of a compound of formula I, or a prodrug thereof, or a pharmaceutically acceptable salt of said compound or prodrug, effective in treating such disorders.

This invention includes prodrugs of compounds of formula I having free amino, amido, hydroxy or carboxylic groups. Prodrugs are understood to comprise an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, by way of example and not of limitation, 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Prodrugs are also understood to include carbonates, carbamates, amides and alkyl esters which are covalently bonded to the above substituents of formula I through the carbonyl carbon prodrug sidechain. Prodrugs also include compounds in which the secondary amine and its β-hydroxy when taken together form a group of the formula

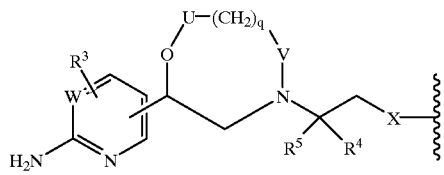

wherein $R^3$, $R^4$, $R^5$ and X are as defined above for formula I, q is 0 to 6, and U and V are independently carbonyl, methylene, $SO_2$ or $SO_3$, wherein methylene is optionally substituted with hydroxy.

This invention further includes intermediates of the structure:

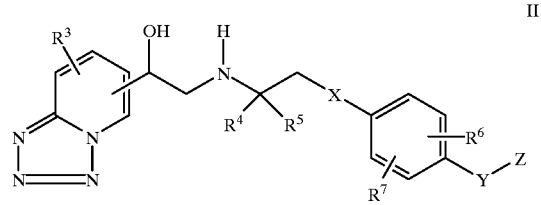
II

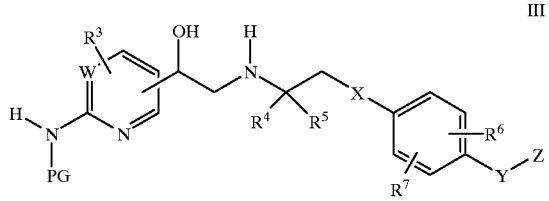
III

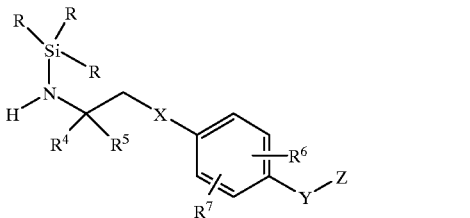
VIIa

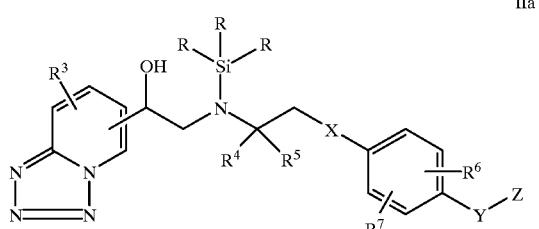
IIa and

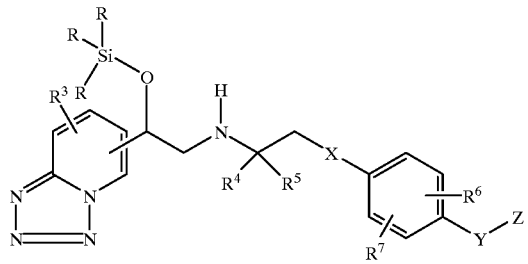
-continued wherein:
PG is a conventional protecting group,
R is an alkyl group;
$R^1$, $R^4$ and $R^5$ are independently hydrogen or $(C_1-C_6)$ alkyl;
$R^3$, $R^6$ and $R^7$ are independently hydrogen, halogen, $(C_1-C_6)$alkyl, nitro, cyano, trifluoromethyl, $SO_2R^8$, $SO_2NR^9R^{10}$, $NR^9R^{10}$, $COR^{11}$, $CO_2R^9$, $(C_1-C_6)$alkoxy, $NR^6SO_2R^8$, $NR^9COR^{11}$, $NR^9CO_2R^9$ or $OR^9$;
$R^8$ is independently $(C_1-C_6)$alkyl or $(C_1-C_6)$alkoxy $(C_1-C_6)$alkyl;
$R^9$ and $R^{10}$ are independently hydrogen, $(C_1-C_6)$alkyl, cycloalkyl$(C_3-C_8)$, or $(C_1-C_6)$alkoxy$(C_1-C_6)$alkyl;
$R^{11}$ is independently hydrogen, $(C_1-C_6)$alkyl, $NR^9R^{10}$, $(C_3-C_8)$cycloalkyl, or $(C_1-C_6)$alkoxy$(C_1-C_6)$alkyl, wherein $R^9$ and $R^{10}$ are as defined above;
W is N, CH, or, when $R^3$ is bonded to W, $CR^3$ wherein $R^3$ can be any of the values listed above for $R^3$ in addition to H;
X and Y are independently a direct link, oxygen, sulfur, or $NR^1$ wherein $R^1$ is as defined above;
Z is $(CH_2)_mOR^9$, $(CH_2)_nCOR^{11}$, $(CH_2)_nSO_2NR^9R^{10}$, $(CH_2)_n-NR^9SO_2R^8$, $(CH_2)_nP(O)(OR^1)(OR^2)$, $(CH_2)_n-O-(CH_2)_mCOR^{11}$, $(CH_2)_n-O-(CH_2)_mP(O)(OR^1)(OR^2)$, $(CH_2)_n-O-(CH_2)_mSO_2NR^9R^{10}$, or $(CH_2)_n-O-(CH_2)_m-NR^9SO_2R^8$ wherein $R^1$, $R^2$, $R^8$, $R^9$, $R^{10}$ and $R^{11}$ are as defined above;
m is 1 to 6; and
n is 0 to 6, provided that if Y is O or S, n is not 0, as further disclosed in detail hereafter.

It will be appreciated by those skilled in the art that compounds of formula I contain at least one chiral center, and possibly two chiral centers when $R^4$ and $R^5$ are different. Accordingly compounds of formula I may exist in, and be isolated in, optically-active and racemic forms. SOme compounds may exhibit polymorphism. It is to be understood that the present invention encompasses any racemic, optically-active, polymorphic or stereoisomeric form, or mixtures thereof, which form possesses properties useful in the treatment of the utilities noted herein, it being well known in the art how to prepare optically-active forms (for example, by resolution of the racemic form by recrystallization techniques, by synthesis from optically-active starting materials, by chiral synthesis, or by chromatographic separation using a chiral stationary phase) and how to determine efficacy for the treatment of the said utilities by the standard tests described hereinafter. In general, (R)-stereochemistry is preferred at all chiral centers in the compounds of this invention.

In this specification the terms "alkyl" and "alkoxy" include both straight and branched chain radicals, but it is to be understood that references to individual radicals such as "propyl" or "propoxy" embrace only the straight chain "normal") radical, branched chain isomers such as "isopropyl" or "isopropoxy" being referred to specifically.

The term "halo", as used herein, unless otherwise indicated, includes chloro, fluoro, bromo and iodo.

The term "treating" as used herein includes preventative as well as disease remitative treatment.

Particular values of $(C_1-C_6)$alkyl include methyl, ethyl, propyl, isopropyl, butyl, isobutyl, t-butyl, pentyl, isopentyl, and hexyl.

Particular values of $(C_1-C_6)$alkoxy include methoxy, ethoxy, propoxy, isopropoxy, butoxy, isobutoxy, t-butoxy, pentoxy, isopentoxy, and hexoxy.

Particular values of $(C_3-C_8)$cycloalkyl include cyclopropyl, cyclobutyl, cyclopentyl, cyclohexyl, and cycloheptyl.

More particular values of $(C_1-C_6)$alkyl include the values of $(C_1-C_3)$alkyl, including methyl, ethyl, propyl, and isopropyl.

More particular values of $(C_1-C_6)$alkoxy include the values of $(C_1-C_3)$alkoxy, including methoxy, ethoxy, propoxy, and isopropoxy.

DETAILED DESCRIPTION

Compounds of formula I can be made by processes which include processes known in the chemical arts for the production of other compounds. Such processes for the manufacture of a compound of formula I as defined above are provided as further features of the invention and are illustrated by the following procedures in which the meanings of generic radicals are as given above unless otherwise defined. The processes can be effected, generally:

(a) for a compound of formula I wherein W is CH and $R^1$ and $R^2$ are H, by reducing a compound of formula II

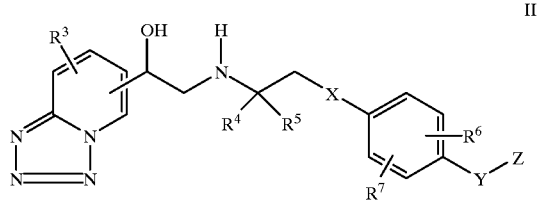

with an appropriate reducing agent. The reaction is conducted employing a reducing agent as known in the art such as stannous chloride, zinc chloride, or hydrogen in the presence of (e.g., 10%) palladium-on-carbon catalyst. The reaction is typically implemented by refluxing in a polar solvent such as a lower alcohol, for example methanol or ethanol.

(b) for a compound of formula I wherein $R^1$ and $R^2$ are H, by deprotecting a compound of formula III

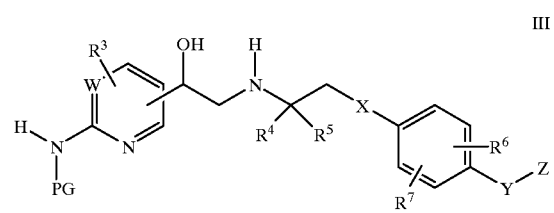

wherein PG is a (conventional) protecting group, preferably a $(C_1-C_6)$acyl (for example, acetyl), a benzyloxycarbonyl (Cbz) or t-butoxycarbonyl (BOC) group, as known in the art. The reaction can be implemented conventionally by hydrogenation, or with a deprotecting reagent such as an acid (e.g., trifluoroacetic acid or a mineral acid such as HCl) in aqueous/alcoholic solvent medium.

(c) for a compound of formula I wherein Z terminates in a carboxylic acid moiety (i.e., the free acid), by hydrolyzing a compound of formula I which is a corresponding $(C_1-C_6)$alkyl ester to the said free acid. The reaction can be conducted conventionally employing a base such as an alkali metal hydroxide in at least a stoichiometric amount, and preferably in excess (e.g., up to a base:compound molar ratio of 5:1), at reflux in aqueous/lower alcohol solvent medium or with an excess of mineral acid in water.

(d) for a compound of formula I wherein Z terminates in a mono- or di-substituted amide moiety, by treating a compound of formula I which is a corresponding $(C_1-C_6)$alkyl ester with a corresponding mono- or di-substituted amine. The reaction can be implemented as a one-step displacement conventionally, at reflux in aqueous/lower alcohol solvent medium.

(e) for a compound of formula (I) wherein $R^1$ and/or $R^2$ are other than H, by treating a compound of formula XXX

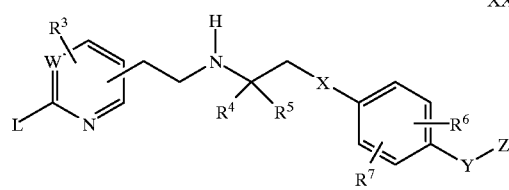

wherein L is a displaceable group, with a corresponding amine of formula $HNR^1R^2$. The reaction is typically conducted in a lower alcohol at reflux.

Methods (c) and (d) are further discussed in Reaction Scheme 5 below.

If they are not commercially available, the necessary starting materials for the above procedures may be made by procedures which are selected from standard organic chemical techniques, techniques which are analogous to the synthesis of known compounds, or techniques which are analogous to the above described procedures or the procedures described in the examples. In particular, the processes and products of the present invention are illustrated in the following reaction schemes wherein, unless otherwise indicated, all variables are as previously defined.

SCHEME 1
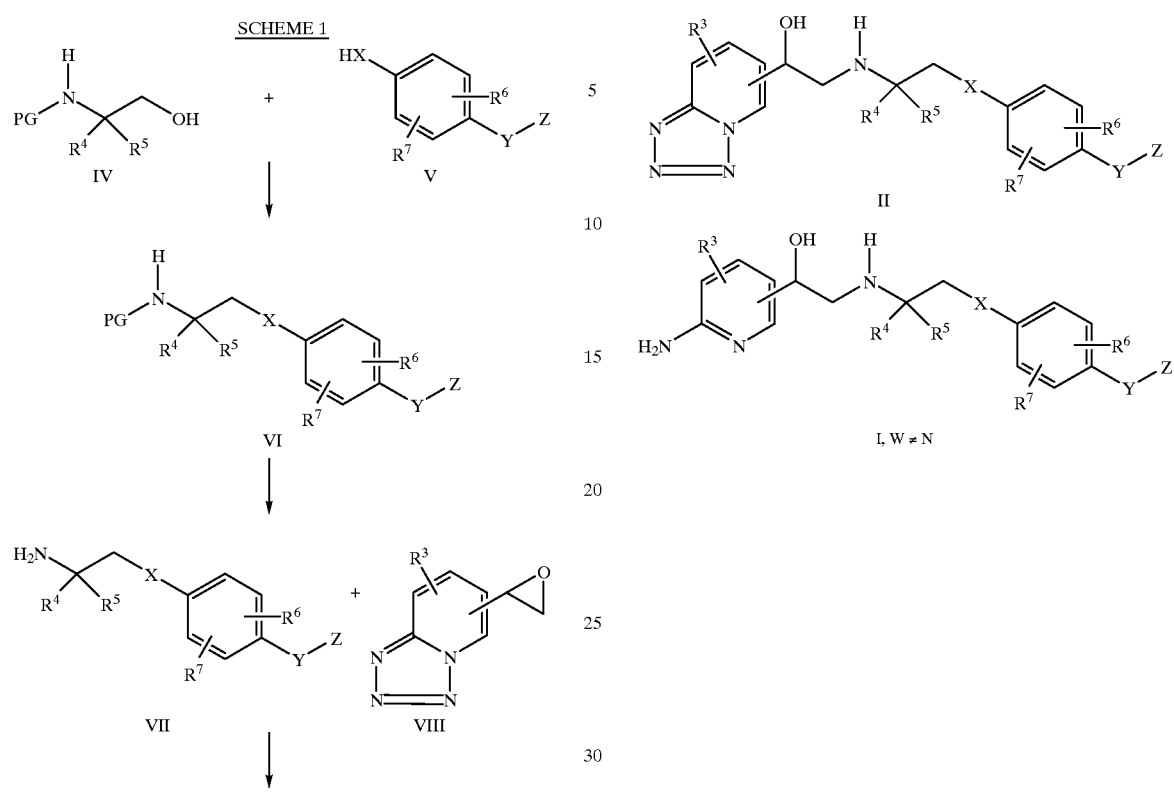
SCHEME 2
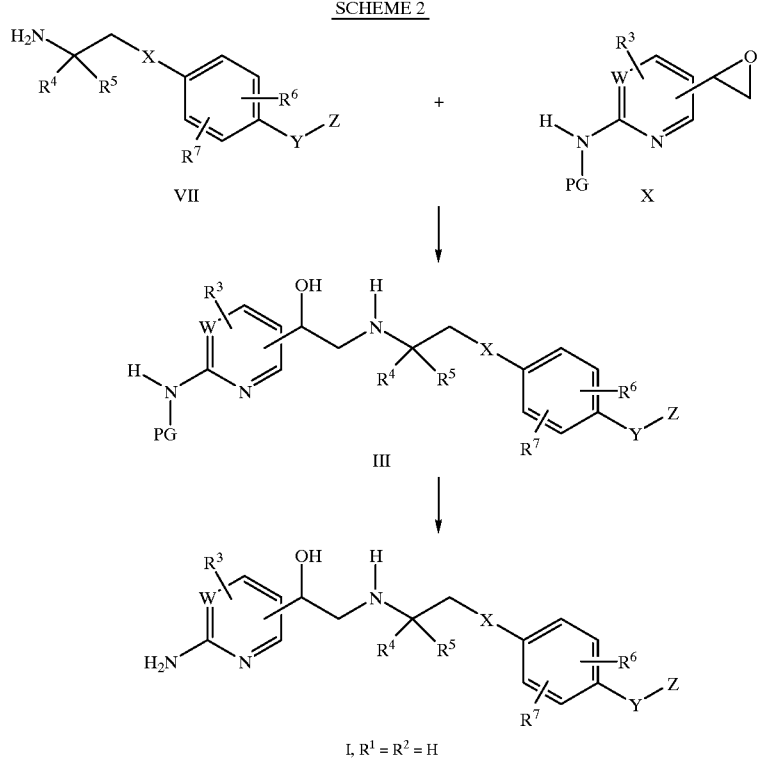

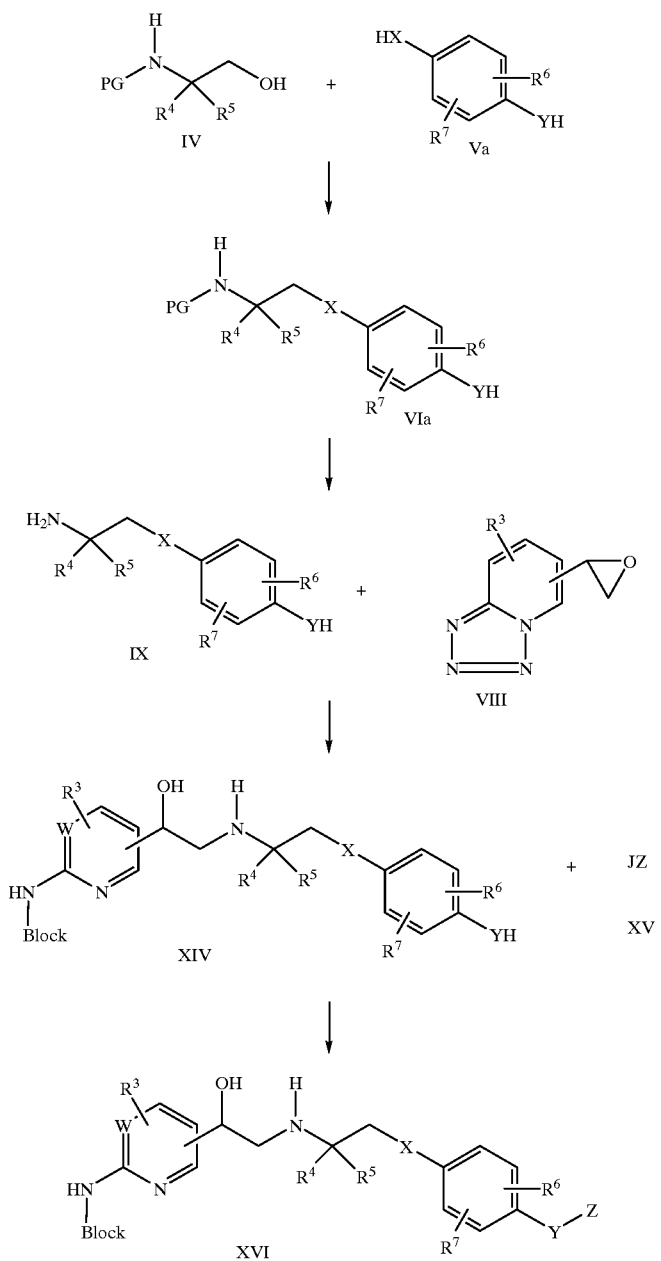

SCHEME 4
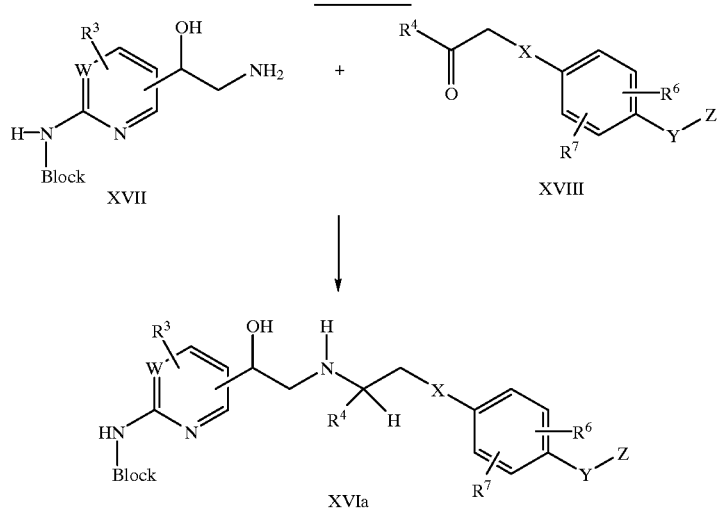
SCHEME 5
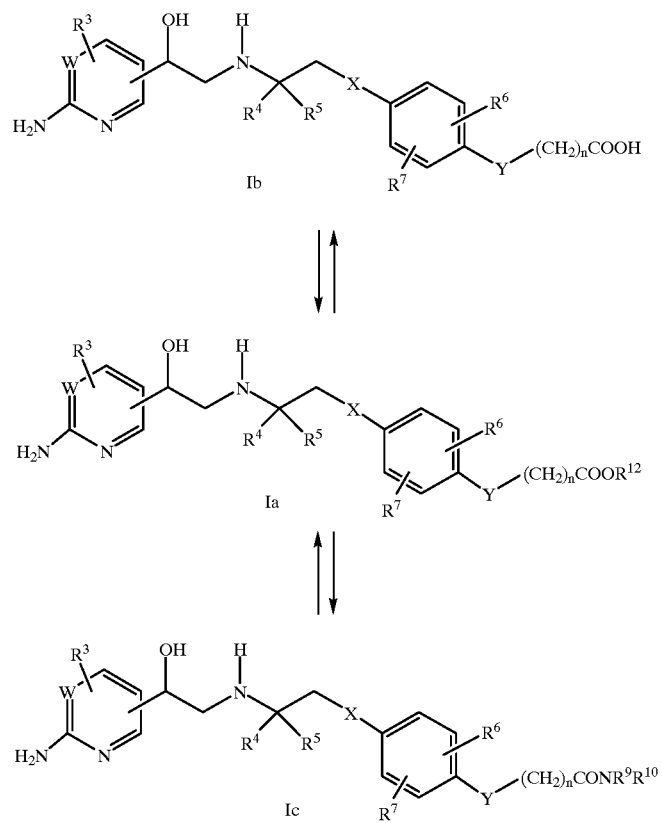

SCHEME 6
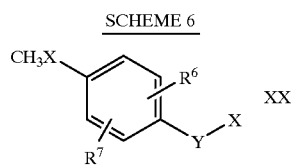
XX
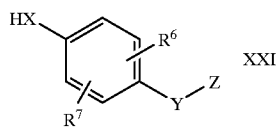
XXI
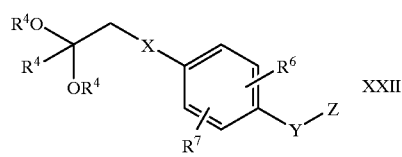
XXII
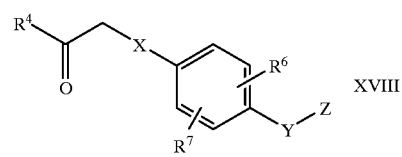
XVIII
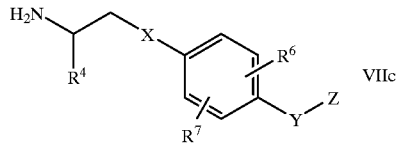
VIIc
SCHEME 7
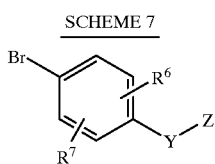
XXIII
-continued
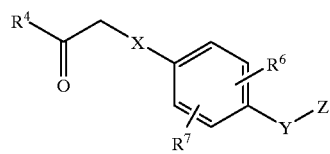
XVIII
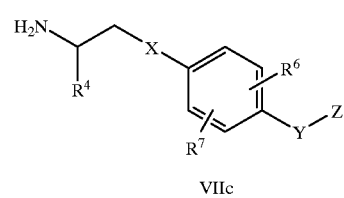
VIIc
SCHEME 8

SCHEME 9

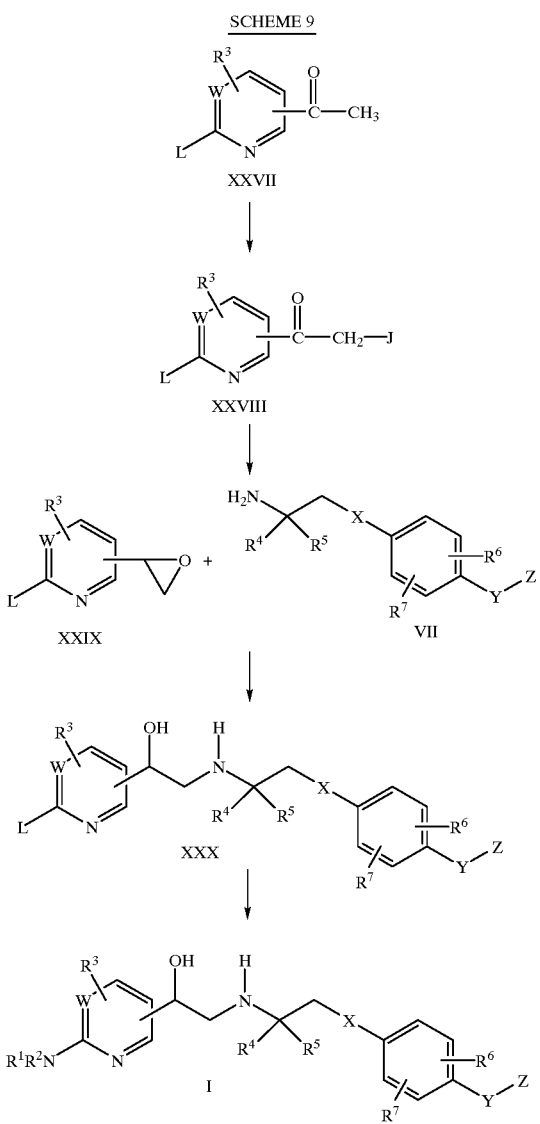

In the discussion which follows, common chemical acronyms and abbreviations have been used: BOC (tert-butoxycarbonyl); Cbz (benzyloxycarbonyl); THF (tetrahydrofuran); DMF (dimethylformamide); DMSO (dimethylsulfoxide); TFA (trifluoroacetic acid). "Lower" as used herein (for example, when referring to a lower alkyl group or a lower alkanol) means ($C_1$–$C_3$).

Preparation of a tetrazole of formula II (and its conversion to a compound of formula I) is illustrated in Scheme 1. Amino alcohol IV, wherein PG is a standard protecting group such as BOC, Cbz, or an ($C_1$–$C_6$)alkylcarbonyl group, is first dehydratively coupled with compound V in a so-called Mitsunobo reaction to make (protected) product amine VI. The reaction is typically conducted with stirring and at room temperature (or higher if preferred) in the presence of a dehydrating agent such as a stoichiometric quantity of diethylazodicarboxylate and a phosphine, for example triphenylphosphine. The reaction can be implemented in any inert solvent such as THF, benzene, toluene, halogenated hydrocarbons, DMF, or DMSO.

Protected amine VI can then be deprotected as known in the art to yield amine VII, for example with an inorganic acid or organic acid such as TFA in an inert solvent such as a halogenated hydrocarbon (e.g., chloroform or methylene dichloride), at room temperature for a reaction time typically of about 2 to about 8 hours. Alternatively, the protecting group PG can be removed by hydrogenolysis using hydrogen in the presence of a palladium-on-carbon catalyst and in an inert solvent such as a lower alcohol or DMF. The hydrogenolysis is typically implemented anywhere from room temperature up to about 90° C.

The amine of formula VII can then be treated with an azo-protected epoxide of formula VIII to yield compound II. This reaction is typically carried out by reacting the amine of formula VII and the epoxide of formula VIII in a polar aprotic solvent such as dimethyl sulfoxide, dimethyl formamide, acetonitrile or a lower alkanol such as ethanol, isopropanol or butanol, at a temperature from about –10° C. to about 125° C.

A preferred modification of the above reaction involves pretreatment of the amine of formula VII with an N-(trialkylsilyl)acetamide, for example N-(trimethylsilyl)acetamide, to form a silylated compound of the formula VIIa

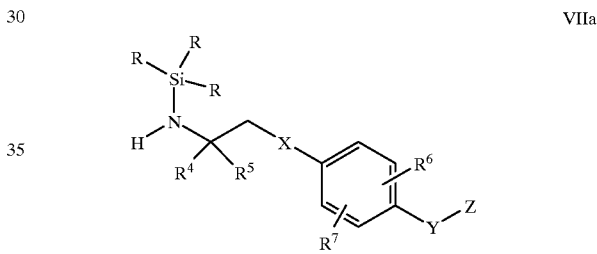

VIIa wherein R is typically a lower alkyl group. This reaction is typically carried out in a polar aprotic solvent such as DMSO, DMF, or acetonitrile, at a temperature from about –10° C. to about 125° C. Preferably, the silylation is carried out at about 25° C. and the reaction with the epoxide is accomplished at about 60° C. After silylation is complete, the compound of formula VIIa is reacted with the epoxide of formula VIII, as described above to form the intermediate of formula IIa.

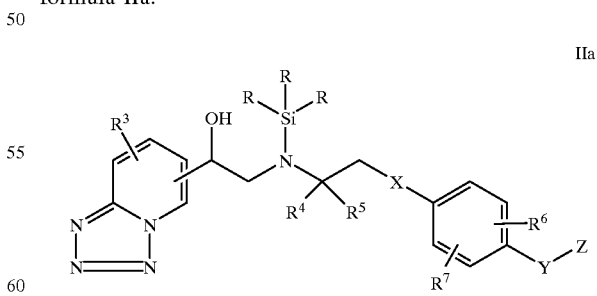

IIa

After the reaction is complete or has otherwise been terminated, the silyl group can be removed by standard means such as by mild acid or base hydrolysis.

It is noted that a silylated derivative of the formula

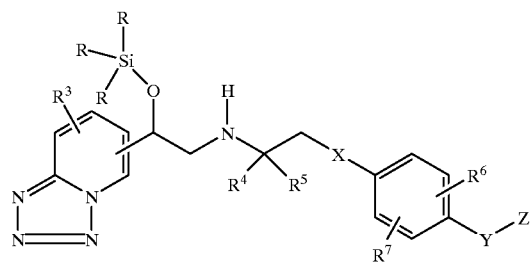

will also be produced, in many cases as the major isomer. The above isomer can also be deprotected by the same standard means.

Following removal of the trialkylsilyl protecting group, compound II can be reduced to convert the tetrazole portion of the molecule to the corresponding pyridyl amine by treatment with a suitable reducing agent, as described above in (a).

Scheme 2 illustrates the preparation of a compound of formula I using a precursor compound of formula III. An epoxide of formula X, wherein W and protecting group PG are as previously defined, can be reacted with amine VII under standard conditions, for example using a polar solvent such as a lower alcohol and implementing the reaction at reflux, typically for a time between 2 and 8 hours. In a preferred embodiment, amine VII is first silylated as described above to make a silylated amine compound of formula VIIa above prior to treating it with epoxide X.

Scheme 3 illustrates the preparation of a compound of formula XVI which is generic to both intermediates of formulae II and III when Y is O, S, or NH. Amino alcohol IV may first be reacted with compound Va, as described for the reaction of amino alcohol IV with compound V for Scheme 1. If X and Y are the same, then the YH moiety need not be protected by pre-reacting with a blocking reagent. If X and Y are different, however, then protecting the YH moiety by standard means, for example by pre-reacting it with an aromatic or aliphatic carboxylic acid, is preferred. De-protection by standard means (e.g. alkaline hydrolysis) can then be effected at essentially any point prior to reacting with compound XV (JZ), described below. The product, compound VIa, can then be de-protected as described for compound VI, Scheme 1, thereby yielding compound IX. Compound IX can be reacted with azo-protected epoxide VIII, as described for the reaction of compounds VII and VIII, Scheme 1. Compound XVI may then be made by reacting compounds XIV and XV, wherein J is a leaving group such as chloro, bromo, or iodo. It is understood that for compound XIV, when W is CH, the "block" moiety attached to the amino group is in the form of a protecting azo group completing a fused tetrazole moiety and compound XVI is then the same as compound II. Or, when W is CH or N, the "block" moiety can additionally be any conventional protecting group, defined hereinbefore as "PG", and structure XVI is then the same as compound III. In either case compounds XIV and XV can be reacted in an inert aprotic solvent such as DMF, DMSO, or toluene and in the presence of a base such as an alkali metal hydride or carbonate (for example sodium hydride or potassium carbonate). The reaction is allowed to proceed typically at ambient temperature and for a period of 1 to 8 hours.

Scheme 4 illustrates the preparation, via reductive amination, of compound XVIa, a subset of formula XVI wherein at least one of $R^4$ and $R^5$ is H and the other of $R^4$ and $R^5$ is H or $(C_1-C_6)$alkyl. Amine XVII and ketone (or aldehyde if $R^4$ is H) XVIII are reacted to produce a compound of formula XVIa. This reaction is typically carried out in the presence of a reducing agent such as sodium cyanoborohydride, sodium triacetoxyborohydride, sodium borohydride, hydrogen and a metal catalyst, zinc and hydrochloric acid, or borane dimethyl sulfide followed by treatment with formic acid. It is generally conducted at temperatures from about −60° C. to about 50° C. Suitable reaction inert solvents for this reaction include lower alcohols (e.g., methanol, ethanol and isopropanol), acetic acid, chlorinated hydrocarbon solvents (e.g., methylene chloride, chloroform, 1,2 dichloroethane) and THF. Preferably, the solvent is 1,2-dichloroethane, the temperature is about 25° C., and the reducing agent is sodium triacetoxyborohydride.

Scheme 5 illustrates the preparation of free acids and amides of formulae Ib and Ic from compounds of formula Ia, as set forth in (c) and (d) above. The use of formulae Ia, Ib, and Ic in Scheme 5 is exemplary. Compounds of formulae Ib and Ic are, respectively, compounds of formula I in which Z is $(CH_2)_n CO_2H$ and $(CH_2)_n COR^{11}$ wherein $R^{11}$ is $NR^9R^{10}$. Scheme 5 applies equally to compounds analogous to formula Ib in which Z is $(CH_2)_n$—O—$(CH_2)_m CO_2H$, and to compounds analogous to formula Ic in which Z is $(CH_2)_n$—O—$(CH_2)_m COR^{11}$ where $R^{11}$ is $NR^9R^{10}$, and $R^9$, $R^{10}$, n and m are as previously defined. Compounds of formula Ia are intermediates corresponding to formula I except that the value corresponding to Z is $(CH_2)_n CO_2R^{12}$ wherein $R^{12}$ is an alkyl group, typically $(C_1-C_6)$alkyl, although other replaceable groups such as $(C_3-C_8)$ cycloalkyl can also be employed. Intermediates corresponding to formula Ia except that the value corresponding to Z is $(CH_2)_n$—O—$(CH_2)_m CO_2R^{12}$ are also useful for making compounds according to the invention. Intermediate compounds of formula Ia are prepared by the methods of Schemes 1, 2, and 3. The transformations depicted in Scheme 5 may be accomplished by methods well known to those skilled in the art. It is noted that the reaction conditions can be adapted so the reverse reactions are favored, though implementation of such conditions is less likely since the free acids are preferred.

In the above discussion pertaining to Scheme 5, compounds of formula Ia have been presented as intermediates. It is noted that compounds of formula Ia are esters which are active compounds in their own right, however. Such formula Ia esters have been separately claimed in application Ser. No. 08/945,552, filed of even date herewith.

Referring to Scheme 5, compounds of formula Ia can be converted into carboxylic acids of formula Ib by treatment with an acid or a base. Examples of suitable bases for the reaction are: sodium hydroxide (NaOH), potassium hydroxide (KOH), and lithium hydroxide. Suitable acids for the reaction include: hydrochloric acid (HCl), hydrobromic acid and sulfuric acid. Preferably, the base is potassium hydroxide. The solvent for the aforesaid process is typically a lower alkanol, hexane, DMF, toluene and/or water. The lower alkanol can be methanol, ethanol, propanol or butanol. The reaction temperature may range from about 0° C. to about 100° C. Preferably, the temperature is about 25° C.

Alternatively, compounds of formula Ia can be converted into amides of formula Ic by treatment of an ester of formula Ia with an amine of the formula $R^9R^{10}NH$. Usually, a polar protic solvent such as a lower alkanol is used, and the reaction is run at a temperature from about 0° C. to about 125° C. for about 0.5 to about 24 hours. Suitable solvents include lower alcohols, and mixtures thereof with toluene, cyclohexane, DMF and methylene chloride. Preferably, the reaction is conducted in methanol at about 65° C. for about 3 to about 24 hours.

Scheme 6 refers to the preparation of compounds of formulae VII wherein at least one of $R^4$ and $R^5$ is H, and XVIII wherein X is O or S. Compounds of formula VII wherein at least one of $R^4$ and $R^5$ is H are labeled as VIIc in Scheme 6. For exemplification only, $R^4$ is illustrated as the variable which can assume values other than H, although it is to be understood that $R^5$ can be the variable as well. Compounds of formulae VIIc and XVIII are starting materials for the synthesis, respectively, of intermediates of formulae II and III in Schemes 1 and 2, and of formula XVIa in Scheme 4, which intermediates can in turn be used to make compounds of formula I.

Referring to Scheme 6, compounds of formula VIIc are made by reductive amination of a compound of formula XVIII. The conditions for reductive amination are as described above for the conversion of a ketone (or aldehyde, as appropriate) of formula XVIII to a compound of formula XVIa in Scheme 4, with the exception that the amine used is ammonia or an acid addition salt thereof, instead of the amine of formula XVII.

Compounds of formula XVIII can be made in three steps beginning with compounds of the formula XX.

Compounds of the formula XX are first converted to thiols or phenols of the formula XXI by treatment of an ether (when X is O) or a thioether (when X is S) of formula XX with boron tribromide. Suitable solvents for the aforesaid reaction are non-polar aprotic solvents such as methylene chloride, toluene, chloroform, or carbon tetrachloride. Preferably, the solvent is methylene chloride. The temperature of the reaction may range from about −78° C. to about 20° C. during the reaction with boron tribromide. It is preferably about 0° C.

The thiol or phenol of formula XXI so formed is converted into a ketal or acetal of the formula XXII by treatment with a compound of the formula

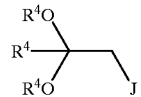

wherein J is chloro, bromo or iodo, in the presence of a base. Preferably, the thiol or phenol of formula XXI is first converted into an anion by reaction with a base. Examples of appropriate bases include sodium hydride and potassium t-butoxide. The preferred base is sodium hydride (NaH). Examples of suitable solvents for the aforesaid process include polar aprotic solvents such as dimethyl formamide, dimethylsulfoxide, and sulfolane. Preferably, the solvent is dimethyl formamide.

The temperature for the aforesaid reaction is in the range of about −10° C. to about 100° C. Preferably, the temperature is 30° C.

The ketal or acetal of formula XXII so formed is converted into the corresponding compound of formula XVIII by reaction with an acid. Typically, this reaction is conducted at a temperature in the range of about 10° C. to about 100° C. Examples of appropriate acids for the aforesaid process are hydrochloric, hydrobromic and sulfuric acids. Preferably, the acid is hydrochloric acid. Suitable solvents for the aforesaid process include polar solvents such as acetone and/or water. Preferably, the solvent is acetone.

Scheme 7 refers to the preparation of compounds of the formulae VIIc and XVIII wherein X is a direct link and at least one of $R^4$ and $R^5$ is H. with the remaining member of $R^4$ and $R^5$ being H or $(C_1–C_6)$alkyl. Again, the single variable value $R^4$ is shown for purposes of illustration. Compounds of the formulae VIIc and XVIII are starting materials for the synthesis of corresponding intermediates useful in the invention as illustrated in Schemes 1, 2 and 4.

Compounds of formula XVIII, wherein X is a direct link, can be used to form intermediates of formula XVIa according to the processes of Scheme 4.

Compounds of the formula VIIc, wherein X is a direct link, can be used to form corresponding compounds of formula I according to the processes of Schemes 1 and 2.

Referring to Scheme 7 (wherein X is a direct link), a compound of formula XVIII can be converted into a compound of formula VIIc by reductive amination of a compound of the formula XVIII with ammonia as described above for Scheme 6.

A compound of formula XVIII can be prepared from a corresponding compound of formula XXIII, by treatment of a compound of the formula XXIII with a tin reagent of the formula $R^4COCH_2Sn(CH_3CH_2CH_2CH_3)_3$ in the presence of palladium (II) acetate and tri-o-tolylphosphine. The tin reagent, $R^4COCH_2Sn(CH_3CH_2CH_2CH_3)_3$, is formed by reaction of tributyltin methoxide with a compound of the formula

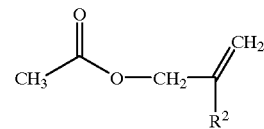

Suitable solvents for the aforesaid process include non-polar solvents such as toluene, benzene and hexane. Preferably, the solvent is toluene. The temperature for the aforesaid process is generally in the range of about 10° C. to about 150° C., and is preferably about 95° C.

Scheme 8 illustrates the preparation of an epoxide of formula VIII, which is used to make an intermediate of formula II and, in turn, a compound of formula I wherein W is CH. The preparation is generally according to methods disclosed in U.S. Pat. Nos. 4,358,455 and 5,019,578. A ketone of formula XXIV can be treated with sodium azide in the presence of an acid such as any of the common mineral acids (e.g., HCl) at reflux in a protic solvent such as aqueous alcohol to yield a tetrazole of formula XXV. Tetrazole XXV can then be treated, preferably with a halogenating agent such as bromine, to yield a corresponding compound of formula XXVI wherein J is a leaving group such as a bromo group. Bromination can be carried out under standard conditions, for example in glacial acetic acid solvent which has been saturated with HBr. Generally the reaction is conducted under chilled (e.g, ice bath) conditions. The compound of formula XXVI can then be converted to the corresponding oxirane VIII under standard conditions, for example by treating compound XXVI with a mild reducing agent (e.g., sodium borohydride, lithium borohydride) at room temperature in an inert solvent such as THF, followed by treatment with a base such as an alkali metal hydroxide in a protic solvent such as an alcohol. A stereospecific reducing agent, such as (R)-alpine borane, may be used to prepare the R-isomer of the oxirane, substantially free of the S-isomer.

Scheme 9 illustrates the synthesis of compounds of formula I when $R^1$ and/or $R^2$ are other than H. A ketone of formula XXVII, wherein L is a group such as F or Cl which can be displaced by a primary or secondary amine, is first treated with a halogenating agent such as bromine to yield a corresponding compound of formula XXVIII wherein J is a leaving group such as a bromo group. Bromination can be effected under standard conditions, for example as described in Scheme 8 for the conversion of tetrazole XXV to compound XXVI. The compound of formula XXVIII can then be converted to the corresponding oxirane XXIX, by the standard procedure also described in Scheme 8. Oxirane XXIX can then be reacted directly with a compound of formula VII, in a polar solvent such as DMSO, DMF, or acetonitrile, at a temperature typically in the range of $-10°$ C. to $125°$ C., thereby yielding a compound of formula XXX. The intermediate of formula XXX can be reacted in a lower alcohol, at reflux (or under pressure, for example if the amine is gaseous), with an amine of formula $HNR^1R^2$ to produce a corresponding compound of formula I.

Conventional methods and/or techniques of purification and separation known to those skilled in the art can be used to isolate the compounds of this invention. Such techniques include all types of chromatography (HPLC, column chromatography using common adsorbents such as silica gel, and thin layer chromatography), recrystallization, and differential (i.e., liquid-liquid) extraction techniques.

Certain of the compounds of formula I; for example those which have free carboxylic acid functionality, form pharmaceutically-acceptable cation salts by reacting the free acid forms with an appropriate base, usually one equivalent, in a co-solvent. Typical bases are sodium hydroxide, sodium methoxide, sodium ethoxide, sodium hydride, potassium methoxide, magnesium hydroxide, calcium hydroxide, benzathine, choline, diethanolamine, piperazine and tromethamine. The salt is isolated by concentration to dryness or by addition of a non-solvent. In many cases, salts are preferably prepared by mixing a solution of the acid with a solution of a different salt of the cation (sodium or potassium ethylhexanoate, magnesium oleate), employing a solvent (e.g., ethyl acetate) from which the desired cationic salt precipitates, or can be otherwise isolated by concentration and/or addition of a non-solvent.

The acid addition salts of the compounds of the present invention are readily prepared by reacting the base forms with the appropriate acid. When the salt is of a monobasic acid (e.g., the hydrochloride, the hydrobromide, the p-toluenesulfonate, the acetate), the hydrogen form of a dibasic acid (e.g., the hydrogen sulfate, the succinate) or the dihydrogen form of a tribasic acid (e.g., the dihydrogen phosphate, the citrate), at least one molar equivalent and usually a molar excess of the acid is employed. However, when such salts as the sulfate, the hemisuccinate, the hydrogen phosphate or the phosphate are desired, the appropriate and exact chemical equivalents of acid will generally be used. The free base and the acid are usually combined in a co-solvent from which the desired salt precipitates, or can be otherwise isolated by concentration and/or addition of a non-solvent.

The amino acid prodrugs of this invention may be prepared by conventional peptide coupling reactions coupling a free amino or carboxylic group of the compound of formula I with an amino acid or a polypeptide, e.g. dipeptide, chain. The coupling reaction is generally conducted at a temperature of about $-30°$ to about $80°$ C., preferably about $0°$ to about $25°$ C. Suitable coupling reagents are usually present, such as dicyclohexylcarbodiimide with hydroxybenzotriazole (HBT), N-3-dimethylaminopropyl-N'-ethylcarbodiimide with HBT, 2-ethoxy-1-ethoxycarbonyl-1,2-dihydroquinoline, carbonyl diimidazole with HBT, or diethylphosphoryl-cyanide. The reaction is generaly conducted in an inert solvent such as acetonitrile, methylene chloride, chloroform, dimethylformamide, dioxane, tetrahydrofuran, dimethoxyethane, or water, or a mixture of two or more such solvents.

Ester, carbonate or carbamate prodrugs of this invention may be prepared by reaction of a free hydroxyl or amino group of the compound of formula I with an 5 activated carbonyl containing molecule such as acetyl chloride or ethyl chloroformate.

The reaction can be carried out neat or in the presence of a reaction inert solvent such as methylene chloride, at a temperature from about $-78°$ to about $100°$ C. Alcohols can also be reacted with cyanogen chloride in the presence of a Lewis acid to form carbamates.

Prodrugs in which the secondary amine and its β-hydroxy, taken together, form a group of the formula

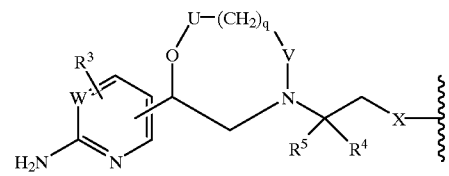

are formed by methods analogous to those described in U.S. Pat. No. 4,593,023, European Patent Application 170,135A published on Jul. 21, 1984 and U.S. Pat. No. 4,607,033.

When treating any of the conditions, disorders and/or diseases previously disclosed herein, generally satisfactory results are obtained when the compounds of the formula (I), prodrugs, or pharmaceutically acceptable salts thereof (hereinafter also referred to herein as "active ingredients or compounds") are administered to mammals, including man, via either the oral or the parenteral route. Administration by the oral route is preferred, being more convenient and avoiding the possible pain and irritation of injection.

However, in circumstances where the patient cannot swallow the medication, or absorption following oral administration is impaired, as by disease or other abnormality, it is essential that the drug be administered parenterally. By either route, the dosage is in the range of about 0.01 to about 100 mg/kg body weight of the subject per day, preferably about 0.1 to about 50 mg/kg body weight per day, administered singly or as a divided dose. However, the optimum dosage for the individual subject being treated will be determined by the person responsible for the treatment, generally smaller doses being administered initially and thereafter increments made to determine the most suitable dosage. This will vary according to the particular compound employed and with the subject being treated.

The compounds of the present invention are used in combination with a pharmaceutically acceptable carrier or diluent. Suitable pharmaceutically-acceptable carriers include inert solid fillers or diluents and sterile aqueous or organic solutions. The active compound will be present in such pharmaceutical compositions in amounts sufficient to provide the desired dosage amount in the range described above. Thus, for oral administration the compounds can be combined with a suitable solid or liquid carrier or diluent to form capsules, tablets, powders, syrups, solutions, suspensions and the like. The pharmaceutical compositions may, if desired, contain additional components such as flavorants, sweeteners, excipients and the like.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

These active compounds may also be administered parenterally. For parenteral administration the compounds can be combined with sterile aqueous or organic media to form injectable solutions or suspensions. SOlutions or suspensions of these active compounds can be prepared in water suitably mixed with a surfactant such as hydroxypropylcellulose. Dispersions can also be prepared in sesame or peanut oil, ethanol, water, polyol (e.g., glycerol, propylene glycol and liquid polyethylene glycol), suitable mixtures thereof, vegetable oils, N-methyl glucamine, polyvinylpyrrolidone and mixtures thereof in oils as well as aqueous solutions of water-soluble pharmaceutically acceptable salts of the compounds. Under ordinary conditions of storage and use, these preparations contain a preservative to prevent the growth of microorganisms. The injectable solutions prepared in this manner can then be administered intravenously, intraperitoneally, subcutaneously, or intramuscularly, with intramuscular administration being the preferred parenteral route in man.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi.

The effective dosage of the active ingredient employed may vary depending on the particular compound employed, the mode of administration, the condition being treated and the severity of the condition being treated.

As a consequence of their action in reducing body fat (lipolysis) the compounds of the present invention possess utility for increasing lean meat deposition and/or improving the lean meat to fat ratio in edible animals including poultry and ungulate animals such as swine, cattle, sheep, and goats. Compounds of formula I can additionally be used for the treatment of obese household pets, for example companion animals such as dogs and cats. The administration of a compound of formula I can be effected orally or non-orally, for example by injection. An amount of a compound of formula I is administered such that an effective dose is received, generally a daily dose which, when administered orally to an animal is usually between 0.01 and 100 mg/kg of body weight, preferably between 0.1 and 50 mg/kg of body weight. Conveniently, the medication can be carried in the drinking water so that a therapeutic dosage of the agent is ingested with the daily water supply. The agent can be directly metered into drinking water, preferably in the form of a liquid, water-soluble concentrate (such as an aqueous solution of a water soluble salt).

Conveniently, the active ingredient can also be added directly to the feed, as such, or in the form of an animal feed supplement, also referred to as a premix or concentrate. A premix or concentrate of therapeutic agent in a carrier is more commonly employed for the inclusion of the agent in the feed. Suitable carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective carrier is the respective animal feed itself; that is, a small portion of such feed. The carrier facilitates uniform distribution of the active materials in the finished feed with which the premix is blended. It is important that the compound be thoroughly blended into the premix and, subsequently, the feed. In this respect, the agent may be dispersed or dissolved in a suitable oily vehicle such as soybean oil, corn oil, cottonseed oil, and the like, or in a volatile organic solvent and then blended with the carrier. It will be appreciated that the proportions of active material in the concentrate are capable of wide variation since the amount of agent in the finished feed may be adjusted by blending the appropriate proportion of premix with the feed to obtain a desired level of therapeutic agent.

High potency concentrates may be blended by the feed manufacturer with proteinaceous carrier such as soybean oil meal and other meals, as described above, to produce concentrated supplements which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound according to the invention. The mixtures are thoroughly blended by standard procedures, such as in a twin shell blender, to ensure homogeneity.

If the supplement is used as a top dressing for the feed, it likewise helps to ensure uniformity of distribution of the active material across the top of the dressed feed.

Drinking water and feed effective for increasing lean meat deposition and for improving lean meat to fat ratio are generally prepared by mixing a compound of the invention with a sufficient amount of animal feed to provide from about $10^{-3}$ to 500 ppm of the compound in the feed or water.

The preferred medicated swine, cattle, sheep and goat feed generally contain from 1 to 400 grams of active ingredient per ton of feed, the optimum amount for these animals usually being about 50 to 300 grams per ton of feed.

The preferred poultry and domestic pet feeds usually contain about 1 to 400 grams and preferably 10 to 400 grams of active ingredient per ton of feed.

For parenteral administration in animals, the compounds of the present invention may be prepared in the form of a paste or a pellet and administered as an implant, usually under the skin of the head or ear of the animal in which increase in lean meat deposition and improvement in lean mean to fat ratio is sought.

In general, parenteral administration involves injection of a sufficient amount of the compounds of the. present invention to provide the animal with 0.01 to 100 mg/kg/day of body weight of the active ingredient. The preferred dosage for poultry, swine, cattle, sheep, goats and domestic pets is in the range of from 0.1 to 50 mg/kg/day of body weight of active ingredient.

Paste formulations can be prepared by dispersing the active compound in a pharmaceutically acceptable oil such as peanut oil, sesame oil, corn oil or the like.

Pellets containing an effective amount of a compound of the present invention can be prepared by admixing a compound of the present invention with a diluent such as carbowax, carnuba wax, and the like, and a lubricant, such as magnesium or calcium stearate, can be added to improve the pelleting process.

It is, of course, recognized that more than one pellet may be administered to an animal to achieve the desired dose level which will provide the increase in lean meat deposition and improvement in lean meat to fat ratio desired. Moreover, it has been found that implants may also be made periodically during the animal treatment period in order to maintain the proper drug level in the animal's body.

The present invention has several advantagous veterinary features. For the pet owner or veterinarian who wishes to increase leanness and trim unwanted fat from pet animals, the present invention provides the means by which this can be accomplished. For poultry and swine raisers, using the method of the present invention yields leaner animals which command higher prices from the meat industry.

The compounds of this invention may be tested for hypoglycemic activity according to the following procedure.

Five to eight week old $C_{57}$ BL/6J-ob/ob mice (obtained from Jackson Laboratory, Bar Harbor, Me.) are housed five per cage under standard animal care practices. After a one week acclimation period, the animals are weighed and 25 microliters of blood is collected via an ocular bleed prior to any treatment. The blood sample is immediately diluted 1:5 with saline containing 2% sodium heparin, and held on ice for glucose analysis. Animals are then regrouped, in groups of five per cage, such that the mean glucose values of the groups are similar, dosed daily for five days with test drug (0.01–100 mg/kg), a positive control such as englitazone or ciglitazone (50 mg/kg p.o.), (U.S. Pat. No. 4,467,902; Sohda et al., Chem. Pharm. Bull., vol. 32, pp. 4460–4465, 1984)), or vehicle. All drugs are administered by oral gavage in a vehicle consisting of 0.25% w/v methyl cellulose. On day 5, the animals are weighed again and bled (via the ocular route) for blood glucose levels. The freshly collected samples are centrifuged for two minutes at 10,000×g at room temperature. The supernatant is analyzed for glucose, for example, by the ABA 200 Bichromatic Analyzer™[1], using the A-gent™ glucose UV reagent system[2] (hexokinase method) using 20, 60 and 100 mg/dl standards. Plasma glucose is then calculated by the equation, $$\text{Plasma glucose (mg/dl)} = \text{Sample value} \times 5 \times 1.67 = 8.35 \times \text{Sample value}$$

where 5 is the dilution factor and 1.67 is the plasma hematocrit adjustment (assuming the hematocrit is 40%).

[1] A registered trademark of Abbott Laboratories, Diagnostics Division, 820 Mission Street, So. Pasadena, Calif. 91030.
[2] A modification of the method of Richterrich and Dauwajder, Schweizerische Medizinische Wochenschrift, 101, 860 (1971).

The animals dosed with vehicle maintain substantially unchanged hyperglycemic glucose levels (e.g., 250 mg/dl), while positive control animals have depressed glucose levels (e.g., 130 mg/dl). The glucose lowering activity of test compounds is expressed in terms of % g lucos e normalization. For example, a glucose level which is the same as the positive control is expressed as 100%.

Selectivity of a compound for $\beta_3$-receptors over $\beta_2$ and $\beta_1$ receptors may be determined u sing the following procedures.

In vitro selectivity may be determined by measurement of cyclic adenosine mono-phosphate (cAMP) accumulation in Chinese hamster ovary cells. Chinese hamster ovary cells uniquely transfected with the gene for the human $\beta_1$, $\beta_2$ or $\beta_3$ receptor are grown to confluence in Ham's F12 media containing 10% fetal bovine serum, 500 $\mu$g/ml Geneticin, 100 U/ml penicillin, 100 $\mu$g/ml streptomycin and 250 ng/ml fungizone. Compounds are prepared as 10 mM stock solutions in DMSO (0.1% DMSO, final concentration), diluted in Ham's F12 media and added to the cells at $10^{-10}$–$10^{-5}$ M along with $10^{-3}$ M isobutylmethylxanthine to inhibit phosphodiesterase activity. The media and cells are the n incubated for 5 minutes at 37° C. At the e nd of this period, the media is aspirated and the cells lysed in 0.01 N HCl. The cellular content of cAMP can then be determined by radio-immunoassay (RIA) using a kit from New England Nuclear. There is a direct correlation between the cellular content of cAMP and the agonism of the $\beta_1$, $\beta_2$, or $\beta_3$ receptor. The non-selective adrenergic agonist, norepinephrine, is included as a positive control at $10^{-5}$M. Data are expressed as fold increase over basal.

In vivo efficacy may be determined by measurement of oxygen consumption and ambulatory activity on male Sprague-Dawley rats. Whole animal oxygen consumption may be measured using an open circuit, indirect calorimeter (Oxymax™, from Columbus Instruments). The Oxymax gas sensors are calibrated with nitrogen ($N_2$) gas and gas mixture (0.5% carbon dioxide ($CO_2$), 20.5% oxygen ($O_2$), 79% $N_2$; Linde Specialty gases) before each experiment. Rats (male, Sprague Dawley, 300–380 g body weight) are placed in sealed chambers (43×43×10 cm) of the calorimeter and the chambers placed in activity monitors. Air flow rate through the chambers is set at 1.6–1.7 l/min. The Oxymax calorimeter software calculates the oxygen consumption (ml/kg/h) based on the flow rate of air through the chambers and difference in oxygen content at inlet and output ports. The activity monitors have 15 infrared light beams spaced one inch apart on each axis; ambulatory activity is recorded when two consecutive beams are broken (repeated interruptions of the same beam are not registered) and the results are recorded as counts. Basal oxygen consumption and ambulatory activity can be measured every 10 minutes for 2.5 to 3 hours. At the end of the basal period, the chambers are opened and the test compound (0.01 to 100 mg/kg, prepared in water or other suitable vehicle) or an equivalent volume of vehicle is administered by oral gavage. Oxygen consumption and ambulatory activity can be measured every 10 minutes for an additional three hours post-dosing. Percent change in oxygen consumption may be calculated by averaging the post-dosing values for 2.5 hours and dividing by basal oxygen consumption (average of the predosing values except the first hour). Oxygen consumption values obtained during time periods where ambulatory activity exceeds 100 counts are excluded from the calculation. Thus, the values represent % change in resting oxygen consumption.

In vivo selectivity for $\beta_1$ and $\beta_2$ adrenergic receptors may be determined by measurements of heart rate, blood pressure and plasma potassium concentration gathered on conscious catheterized rats (male, Sprague Dawley, 300–380 g body weight). To implant catheters rats are anesthetized with pentobarbital (50–60 mg/kg, i.p.) and the left carotid artery is cannulated with PE50 tubing. The catheter is tunneled subcutaneously, exteriorized at the back of the neck, filled with a solution of polyvinylpyrrolidone in heparinized saline, flame-sealed and taped. Experiments are performed 7 days after surgery. On the day of the experiment, the catheters are untaped and flushed with saline. After at least 30 minutes, basal values for heart rate and blood pressure are measured by attaching the catheter to a pressure transducer, the results recorded on a Grass Model 7 polygraph, and a basal blood sample (0.5 ml) is obtained from the arterial catheter. After obtaining basal values, the test compound or vehicle is administered by oral gavage, and blood pressure (measure of $\beta_2$ activity) and heart rate (measure of $\beta_1$ activity) measurements are taken at 15, 30, 45 and 60 minutes and blood samples for potassium determination ($\beta_2$) are obtained at 30 and 60 min. Isoproternol, a non-selective $\beta$-agonist can be tested as a positive control at doses ranging from 0.001 to 1 mg/kg (injected s.c. in saline vehicle). Plasma potassium is determined by flame spectrophotometry. To determine changes, basal values are subtracted from the average of the post dosing values.

Compounds of the formula I also have the effect of reducing intestinal motility and thus find utility as aiding in the treatment of various gastrointestinal disorders such as irritable bowel syndrome, peptic ulceration, esophagitis, gastritis and duodenitis, (including that induced by *H. pylori*), intestinal ulcerations (including inflammatory bowel disease, ulcerative colitis, Crohn's disease and proctitis) and gastrointestinal ulcerations. It has been proposed that the motility of non-sphincteric smooth muscle contraction is mediated by activity at $\beta_3$ adrenergic receptors. The availability of a $\beta_3$ specific agonist, with little activity at $\beta_1$ and $\beta_2$ receptors will assist in the pharmacologic control of intestinal motility without concurrent cardiovascular effects. In vivo activity of the compounds of formula I for the treatment or prevention of intestinal motility disorders can be determined according to the following procedures. Eighteen-hour fasted male Sprague Dawley derived (CD) rats (175–225 grams) are dosed with 0.01–100 mg/kg p.o. of compound or vehicle (distilled water). Thirty minutes after drug administration, the rats are orally dosed with 0.25 ml of a solution of sodium chromate in 0.9% saline containing about 20,000 cpm of $^{51}Cr$ (specific activity 350 mCi/mg Cr). Twenty minutes later, the rats are sacrificed, the gastroesophageal, pyloric, and ileocecal junctions are then ligated, and the stomachs and small intestines removed. The small intestines are then divided into ten equal lengths, and the stomach and each length of intestine assayed for radioactivity with a gamma counter. Gastric emptying rate may then be determined for each rat by comparing the amount of radioactivity in the intestine relative to the total in the intestine plus stomach. In addition, the geometric center of the distribution of the radioactive marker is then used as a measure of the overall transit rate through the stomach and intestine. The geometric center is calculated by summing the products of the fractions of $^{51}Cr$ in each segment times the segment number: geometric center=$\Sigma$ ((fraction of $^{51}Cr$ per segment)×(segment number)). For these calculations the stomach may be considered segment number 0, and the ten intestinal segments as numbers 1 to 10. Thus, a geometric center of 0.0 would indicate that the entire load of $^{51}Cr$ had remained in the stomach. Data from two experiments may be pooled, and statistical evaluations can be made using Dunnett's multiple comparison test.

Alternatively, in groups of 8, overnight4asted male Sprague-Dawley (CD) rats (175–225 grams) may be anesthetized with methoxyflurane. A small abdominal incision is then made, and the pylorus ligated. Immediately after the ligation, a solution of compound or the vehicle (distilled water) is injected into the proximal duodenum. The doses of drug used should be 0.01–100 mg/kg. The incisions can then be closed and the rats can be allowed to recover from the anesthesia. Two hours after the ligation the rats are sacrificed and the gastric fluid collected and cleared by centrifugation. Total volume of secretion can be determined by weight, and acidity can be determined by titration to pH 7.0 with 0.1 N NaOH using an automatic titrator (Radiometer TTT85). The data from two experiments is then pooled. A group of rats treated with 10 mg/kg of the antisecretory histamine $H_2$-receptor antagonist cimetidine may be included in each experiment as a positive control. Statistical evaluations can be made using Student's t-test.

In vitro activity for relaxation of contracted ileum from isolated guinea pig ileum can be determined according to the following procedure. Fresh isolated segments of guinea pig ileum (about 1.5 cm long) are mounted in tissue baths containing Tyrode's physiological salt solution at 30° C. and aerated continuously with $O_2$;$CO_2$ (95%;5%). Tissues are then equilibrated for 60–90 minutes under 4.0 gm tension in order to achieve stable baselines. Histamine is then added to the baths in a cumulative fashion in concentrations ranging from 1 nM to 10 $\mu$M. The maximum tension generated after each addition of histamine is recorded on a Grass Physiograph. The tissues are then washed with several changes of Tyrode's solution, basal tension can be readjusted to 4.0 grams, and a stable baseline is then again obtained. Each tissue may then be exposed to a single concentration of test compound (range 1 nM to 10 $\mu$M) or vehicle and after a 30 minute equilibration period, the histamine does response curve may then be repeated. Results from multiple experiments are standardized (0–100%) to the maximum response of the control tissues and plotted as percent maximum tension versus the log of the histamine concentration in the absence and presence of the drug.

Compounds of formula I can be assessed for antidepressant activity in vivo according to the following procedure.

Male CD1 mice weighing between 20 and 25 g, and Sprague-Dawley rats weighing between 200 and 250 g, may be obtained from Charles River, USA. Compounds of formula I are dissolved in water. The compounds may be administered to mice in a volume of 10 ml $kg^{-1}$, and to rats in a volume 2 ml $kg^{-1}$. Control animals receive the vehicle. Positive test results for the following parameters indicate antidepressant activity.

I. Antagonism of hypothermia induced by reserpine:

Mice are given reserpine (2.5 mg $kg^{-1}$ i.p. dissolved in 1% citric acid). Their rectal temperatures may be measured 3.5 h later. The mice may then be divided into different groups so as to obtain the same mean rectal temperature in each group. Half an hour later (i.e. 4 h after reserpine), the mice are given the vehicle or test drug. Rectal temperature can be measured again 90 min later (i.e. 5 h 30 min after the injection of reserpine) (Bourin et al., *The Value of the Reserpine Test in Psychopharmacology*, Arzneim. Forsch. 33, 1173, (1983)).

II. Antagonism of hypothermia induced by apomorphine:

Half an hour after the mice are placed in individual cages, their rectal temperatures are recorded. The animals should be allocated so as to obtain the same mean rectal temperature in each group. Apomorphine (16 mg $kg^{-1}$ s.c.) can be given 30 min after the test drug or its vehicle. Rectal temperature can be measured again 30 min after the apomorphine treatment (Puech et al, *Antagonism of Hypothermia And Behavioural Response To Apomorphine; A Simple, Rapid And Discriminatinq Test For Screening Antidepressants And Neuroleptics*, Psychopharmacology 75, 84, (1981)).

III. Effect on learned helplessness behavior:

This test is performed basically as described by Giral et al. *Reversal Of Helpless Behaviour In Rats By Putative* $5-HT_{IA}$ *Agonists*. Biol. Psychiat. 23, 237. (1988). Electric foot-shocks are delivered to male albino Sprague-Dawley rats placed in chambers (20×10×10 cm) with Plexiglass® walls and covers. The floors are made of stainless-steel grids (1.5 cm mesh). A constant-current shocker is delivered as 60 scrambled, randomized inescapable shocks (15 s duration, 0.8 mA, every 60+15 s) to the grid floor. Control rats are then placed in identical chambers for 1 h but no shock is administered. All preconditioning trials are performed on day 1 between 9 and 11 a.m. Avoidance training is initiated 48 h (day 3) after inescapable shock in automated two-way shuttle-boxes (60×21×30 cm) with Plexiglass® walls and a floor consisting of stainless-steel rods spaced 1.0 cm apart in order to evaluate escape deficits. Each shuttle-box is divided into two chambers of equal size by a stainless-steel partition, with a gate providing access to the adjacent compartment through a 7×7 cm space. Shuttle-box sessions are performed for 3 consecutive days (days 3, 4 and 5). The animals are placed individually in the shuttle-box and allowed to habituate to the environment for 5 min (for the first session only) and then subjected to 30 trials. The intertrial interval should be 30 s. A light signal, used as a conditioned stimulus, is presented during the first 3 s of each trial. Crossing the gate into the other compartment of the box during this 'conditioned-stimulus only' period (referred to as avoidance response) allows the rats to avoid shocks. A period with conditioned stimulus plus electric foot-shock (0.8 mA) may be presented if an avoidance response does not occur. Crossing the gate into the other compartment during this conditioned stimulus plus shock period is referred to as an escape response. Absence of escape response during the 3-s duration conditioned stimulus plus shock should be considered to be an escape failure.

The rats (n=10 per group) should be treated randomly according to one of the following protocols: the control sample, which receives no shock, and is given vehicle; experimental animals with inescapable shock are treated daily with vehicle or drug. Animals should be treated orally over 5 consecutive days, i.e. 6 h after shock pretreatment on day 1, and then twice per day, a half dose in the morning (30 min before shuttle-box session) and a half dose in the afternoon (except on the 5th day). Statistical analysis can be performed on the mean number of escape failures using a two-way analysis of variance (subjects×sessions) followed by Dunnett's test.

Compounds of formula I also have the effect of bronchial relaxation and increased ciliary motility and thus may be useful in the treatment of airway inflamatory disorders such as asthma and obstructive lung disease. In vitro activity of compounds for the treatment of airway inflamatory disorders can be determined by measurement of guinea-pig bronchial ring relaxation according to the following procedure.

Guinea-pig main bronchial rings are obtained from tri-colored guinea-pigs of either sex (250–350g) anesthetized with urethane (1.25 g $kg^{-1}$, i.p.) and are suspended under an initial tension of 2.0 g in Krebs solution at 37° C. gassed with 95% $O_2$:5% $CO_2$. After 1 h of equilibration, guinea-pig bronchial rings are contracted with acetylcholine ($10^{-3}$ M) and relaxed to maximal relaxation with theophylline ($3\times10^{-3}$ M), then allowed to equilibrate for a further 60 min while they are washed with Krebs solution every 15 min.

Changes in tension are measured isometrically with strain gauges and amplifiers and displayed on a recorder. The composition of the Krebs solution is (mM): NaCl 118.0, KCl 5.4, $CaCl_2$ 2.5, $KH_2PO_4$ 1.2, $MgSO_4$ 1.2, $NaHCO_3$ 25.0 and glucose 11.7

To test effects of test compounds on resting tension, cumulative concentration-response curves are obtained by addition of the test compounds ($10^{-9}$ to $10^{-6}$M) every 10–20 min until a plateau is reached. The relaxant effects of the compounds are expressed as percentages of the maximal relaxation induced by theophylline ($3 \times 10^{-3}$ M).

In vitro activity of the compounds of formula I for prostate disease can be determined according to the following procedures.

Ventral prostates of male Sprague-Dawley rats (300–400 g) anesthetized with diethylether are quickly excised and placed in oxygenated Krebs solution. While maintained at room temperature in this buffer, adherent fatty and connective tissues are removed. The prostates are then suspended in 10-ml organ baths containing Krebs solution warmed to 37° C. and aerated with a mixture of 95% $O_2$ and 5% $CO_2$. The composition of the Krebs solution is 118.4 mM NaCl, 4.7 mM KCl, 1.2 mM $MgSO_4$, 2.5 mM $CaCl_2$, 11.1 mM dextrose, 25.0 mM $NaHCO_3$ and 1.2 mM $KH_2PO_4$, dissolved in distilled and demineralized water. The tissues are attached to isometric force-displacement transducers and isometric contraction is recorded under a loading tension of 0.5 g. Equilibration is undertaken for 1 or 2 hr before the addition of test compounds. Submaximal contractions are first elicited by repeated concentrations of $1 \times 10^{-6}$M phenylephrine until constant responses are obtained. The control and test compound-treated experiments are done in different preparations. A concentration-response curve to cumulate concentrations of phenylephrine or acetylcholine ($10^{-9}$ to $10^{-4}$M) is determined. For testing compounds, a concentration response curve to phenylephrine or acetylcholine is determined in the presence of the β agonists.

In vitro activity of test compounds can also be determined for specific efficacy in human prostate as follows.

Prostatic tissue specimens are obtained from patients with symptomatic BPH, who are undergoing open prostatectomy. Isolated human prostatic tissue is cut into five to eight strips (3 mm wide, 3 mm thick and 15 mm long in each strip). The strips are mounted vertically in organ baths containing 20 ml Krebs-Henseleit solution of the following composition (mM): NaCl 112, KCl 5.9, $MgCl_2$ 1.2, $CaCl_2$ 2, $NaHCO_3$ 25, $NaHPO_4$ 1.2, glucose 11.5. The medium is maintained at 37° C. and at pH 7.4, and is equilibrated with a gas mixture consisting of 95% $O_2$ and 5% $CO_2$. A resting tension of 0.5 g is applied and the responses are recorded isometrically through a force-displacement transducer. The preparations are equilibrated for 90 min before starting the experiments.

Concentration-response curves for phenylephrine or acetylcholine ($10^{-9}$ to $10^{-4}$M) are determined by adding the drug directly to the bathing media in a cumulative fashion. For testing compounds, the prostate strips are incubated in the presence of compound (1 or 10 μM) for 30 minutes before and then phenylephrine or acetylcholine are added to the medium in a cumulative fashion to obtain to the concentration-response curve in the presence of the test compound.

Compounds of the formula I lower triglyceride levels and cholesterol levels and raise high density lipoprotein levels and are therefore of use in combating medical conditions wherein such lowering (and raising) is thought to be beneficial. Thus they may be used in the treatment of hypertriglyceridaemia, hypercholesterolemia and conditions of low HDL (high density lipoprotein) levels in addition to the treatment of atherosclerotic disease such as of coronary, cerebrovascular and peripheral arteries, cardiovascular disease and related conditions.

The active compounds may also be combined with other active ingredients known for use in the treatment of atherosclerosis and related conditions, for example fibrates such as clofibrate, bezafibrate and gemfibrozil; inhibitors of cholesterol biosynthesis such as HMG-CoA reductase inhibitors for example lovastatin, simvastatin and pravastatin; inhibitors of cholesterol absorption for example beta-sitosterol and (acyl CoA;cholesterol acyltransferase) inhibitors for example melinamide; anion exchange resins for example cholestyramine, colestipol or a dialkylaminoalkyl derivatives of a cross-linked dextran; nicotinyl alcohol, nicotinic acid or a salt thereof; vitamin E; and thyromimetics.

Activity of compounds of formula I for dyslipidemia can be determined according to the following procedure. C57BL/6J ob/ob mice (male, 30–40 g body weight, Jackson Lab, Bar Harbor, Me.), housed 5 mice per cage in an environmentally controlled room, can be dosed once daily for 3 weeks with drug (0.01–100 mg/kg, n=15 per group) or vehicle (saline) by oral gavage. Body weight of each mouse can be measured daily and food intake per cage is determined by weighing the amount of food left in the trough. At the end of the study, 24 h after giving the final dose of compound, the mice may be sacrificed by decapitation and blood collected. Plasma concentrations of glucose, free fatty acids and triglyceride can be determined with the VP Super System Autoanalyzer (Abbott, Irving, Tex.).

Activity of compounds of formula I for decrease in body fat can be determined according to the following procedure. $C_{57}BL/6J$ ob/ob mice (male, 30–40 g body weight, Jackson Lab, Bar Harbor, Me. are housed 5 mice per cage in an environmentally controlled room with food (pelleted rodent chow) and water available ad libitum. The compounds or vehicle (water) can be dosed once daily for 3 weeks (0.01–100 mg/kg, n=15 per group) by oral gavage. Body weight of each mouse can be measured daily and food intake per cage determined by weighing the amount of food left in the trough. At the end of the study, 24 h after giving the final dose of compound, the mice are weighed and then killed by cervical dislocation. The epididymal fat pads from each mouse are excised and weighed. The fat versus body weight ration is determined for each mouse using the absolute body weights and the fat pad weights.

A reduction in fat pad weight is indicative of a reduction in total body fat.

The present invention is illustrated by the following Examples. However, it should be understood that the invention is not limited to the specific details of these examples.

EXAMPLE 1

Example 1a—Methyl (4-(2-t-butoxycarbonylaminoethoxy)phenyl) acetate

To a stirred solution of methyl 4-hydroxyphenyl acetate (4.00 g, 24.1 mmol) and triphenylphosphine (9.50 g, 36.1 mmol) in THF (24 mL) were added solutions of 2-(t-butoxycarbonylamino)ethanol (5.80 g, 36.1 mmol) and diethylazodicarboxylate (5.70 mL, 36.1 mmol) in THF (6 mL, each) simultaneously over a 1.5 h period. After an additional 3 h, the reaction was concentrated in vacuo and subjected to flash chromatography (600 g silica gel, 20% ethyl acetate/hexanes) to afford a golden oil, 5.78 g. $^1$H NMR (CDCl$_3$) δ 7.15 (d, 2H), 6.80 (d, 2H), 4.95 (br s, 1H), 3.98 (m, 2H), 3.65 (s, 3H), 3.54 (s, 2H), 3.48 (m, 2H) 1.44 (s, 9H).

Example 1b—Methyl (4-(2-aminoethoxy)phenyl) acetate

To a cooled (5° C.), stirred solution of methyl (4-(2-t-butoxycarbonylaminoethoxy)phenyl) acetate (5.75 g, 18.6 mmol) in dichloromethane (20 mL) was added trifluoroacetic acid (6 mL). The resulting solution was stirred at ambient temperature for 2 h, diluted in ethyl acetate, washed with half-saturated sodium carbonate, brine, dried (Na$_2$SO$_4$) and concentrated in vacuo to afford an orange oil, 3.25 g. $^1$HNMR (CDCl$_3$) δ 7.10 (d, 2H), 6.77 (d, 2H), 3.92 (t, 2H), 3.60 (s, 3H), 2.49 (s, 2H), 3.00 (t, 2H).

Example 1c—Methyl (4-(2-(2(R)-hydroxy-2-tetrazolo[1,5-a]pyridin-6-ylethylamino) ethoxy)-phenyl)acetate A solution of methyl (4-(2-aminoethoxy)phenyl) acetate (0.56 g, 2.71 mmol) and (2R)-(tetrazolo[1,5-a]pyrid-6-yl)oxirane (0.40 g, 2.47 mmol), generated as in Example 1 of U.S. Pat. No. 5,030,640, in methanol (7.5 mL) was heated at reflux temperature for 7 h. Concentration of the reaction solution in vacuo afforded a solid which was subjected to flash chromatography (3% methanol/chloroform) to afford the title compound as a colorless solid, 0.52 g. $^1$H NMR (CDCl$_3$) δ 8.86 (s, 1H), 7.92 (d, 1H), 7.57 (d, 1H), 7.15 (d, 2H), 6.81 (d, 2H), 4.83 (dd, 1H), 4.06 (t, 2H), 3.66 (s, 3H), 3.56 (s, 2H), 3.20–3.02 (m, 3H), 2.76 (dd, 1H).

Example 1d—Methyl (4-(2-(2-(6-aminopyridin-3-yl)-2(R)-hydroxyethylamino)ethoxy)phenyl) acetate A slurry of methyl (4-(2-(2(R)-hydroxy-2-tetrazolo [1,5-a]pyridin-6-ylethylamino)ethoxy)phenyl) acetate (0.51 g, 1.37 mmol) and stannous chloride-dihydrate (0.93 g, 4.12 mmol) in methanol (7 mL) was heated at 60° C. for 3 h. The resulting clear solution was diluted into methylene chloride, washed with one-half saturated aqueous sodium carbonate, brine, dried (Na$_2$SO$_4$) and concentrated in vacuo to a foam, 0.42 g. Flash chromatography (10% methanol/dichloromethane) afforded a colorless solid, 0.22 g; m.p. 90–93° C. $^1$H NMR (CDCl$_3$) δ7.95 (s, 1H), 7.40 (d, 1H), 7.10 (d, 2H), 6.78 (d, 2H), 6.42 (d, 1H), 4.54 (dd, 1H), 4.36 (s, 2H), 4.00 (t, 2H), 3.63 (s, 3H), 3.52 (s, 2H), 3.06–2.92 (m, 2H), 2.86 (dd, 1H), 2.68 (dd, 1H).

Example 1e—(4-(2-(2-(6Aminopyridin-3-yl)-2(R)-hydroxyethylamino)ethoxy)phenyl)acetic acid To a stirred solution of the product of Example 1d, methyl (4-(2-(2-(6-aminopyridin-3-yl)-2(R)-hydroxyethylamino) ethoxy)phenyl)acetic acid (0.11 g, 0.03 mmol), in methanol (6 mL) were added water (1.5 mL) and potassium hydroxide (0.07 g, 1.3 mmol). The resulting solution was allowed to stir at room temperature for 4 h and concentrated in vacuo. The resulting mixture was dissolved in water (2 mL) and the pH adjusted to +5.5 with 1N aqueous hydrochloric acid. The precipitate was filtered and dried at 80° C. in vacuo to afford a colorless solid, 0.10 g; m.p. 233–235° C. $^1$H NMR (DMSO-d6) δ 7.81 (s,1H), 7.33 (d, 1H), 7.13 (d, 2H), 6.86 (d, 2H), 6.40 (d, 1H) 6.00 (br s, 2H), 4.78 (dd, 1H), 4.23 (t, 2H), 3.46 (s, 2H), 3.33 (t, 2H), 3.09 (t, 2H)

EXAMPLE 2

Example 2a—Following the general methodology of example 1a, methyl 4-(2-t-butoxycarbonylaminoethoxy) benzoate was prepared from 2-(BOC-amino)ethanol and methyl 4-hydroxybenzoate; m.p. 85° C.; $^1$H NMR (CDCl$_3$) δ 7.90 (d, 2H), 6.82 (d, 2H), 4.92 (br s, 1H), 4.00 (t, 2H), 3.82 (s, 3H), 3.49 (m, 2H), 1.39 (s, 9H).

Example 2b—Following the general methodology of example 1b, methyl 4-(2-aminoethoxy)benzoate was prepared from the product of Example 2a; m.p. 48° C.; $^1$H NMR (DMSO-d6) δ 7.84 (d, 2H), 6.97 (d, 2H), 3.94 (t, 2H), 3.77 (s, 3H), 2.84 (t, 2H).

Example 2c—Following the general methodology of example 1c, methyl (4-(2-(2(R)-hydroxy-2-tetrazolo [1,5-a] pyridin-6-ylethylamino)ethoxy)phenyl) benzoate was prepared from the product of Example 2b and (2R)-(tetrazolo [1,5-a]pyrid-6-yl)oxirane $^1$H NMR (DMSO-d6) δ 9.10 (s, 1H), 8.10 (d, 1H), 7.90–7.78 (m, 3H), 6.96 (d, 2H), 5.76 (d, 1H), 4.86–4.77 (m, 1H), 4.04 (t, 2H), 3.78 (s, 3H), 2.91 (t, 2H), 2.83 (d, 2H).

Example 2d—Following the general methodology of example 1d, methyl 4-(2-(2-(6-aminopyridin-3-yl)-2(R)-hydroxyethylamino)ethoxy)benzoate was prepared from the product of Example 2c. The product was then combined with 2 equivalents of HCl gas in alcoholic solvent to afford the dihydrochloride salt. m.p. 222–224° C. $^1$H NMR (CDCl$_3$) δ 9.25 (br d, 2H), 8.20 (br s, 2H), 7.96–7.83 (m, 4H), 7.05 (d, 2H), 7.01 (d, 1H), 4.97 (dd, 1H), 4.37 (t, 2H), 3.80 (s, 3H), 3.44–3.10 (m, 4H).

Example 2e—Following the general methodology of example 1 e, 4-(2-(2-(6-aminopyridin-3-yl)-2(R)-hydroxyethylamino)ethoxy)benzoic acid was prepared by hydrolysis of the product of Example 2d. m.p. 218–2190° C. $^1$H NMR (MeOH-d4) δ 8.00 (d, 2H), 7.92 (s, 1H), 7.59 (d, 1H), 7.06 (d, 2H), 6.65 (d, 1H), 4.96 (dd, 1H), 4.40 (t, 2H), 3.58 (t, 2H), 3.32–3.22 (m, 2H).

EXAMPLE 3

Example 3a—Following the general methodology of example 1a, methyl (4-(2-t-butoxycarbonylaminoethoxy) phenyl)propionate was prepared from 2-(BOC-amino) ethanol and 4-hydroxyphenylpropionate, isolated as a colorless oil. $^1$H NMR (CDCl$_3$) δ 7.04 (d, 2H), 6.74 (d, 2H), 4.95 (br s, 1H), 3.94 (t, 2H), 3.62 (s, 3H),3.52–3.40 (m, 2H), 2.84 (t, 2H), 2.54 (t, 2H), 1.40 (s, 9H).

Example 3b—Following the general methodology of example 1b, methyl (4-(2-aminoethoxy)phenyl)propionate was prepared from the product of Example 3a as a colorless oil. $^1$H NMR (CDCl$_3$) δ 7.00 (d, 2H), 6.73 (d, 2H), 3.87 (t, 2H), 3.58 (s, 3H), 2.97 (t, 2H), 2.80 (t, 2H), 2.50 (t, 2H).

Example 3c-Methyl (4-(2-(2(R)-hydroxy-2-tetrazolo[1,5-a] pyridin-6-ylethylamino)ethoxy)phenyl)propionate A solution of methyl (4-(2-aminoethoxy)phenyl) propionate (0.83 mg, 3.70 mmol) and N-trimethylsilylacetamide (0.81 g, 6.2 mmol) in toluene was stirred at ambient temperature for 15 min, then (2R)-(tetrazolo[1,5-a]pyrid-6-yl)oxirane (0.50 g, 3.08 mmol) was added and the resulting mixture was heated at 90° C. for 20 h. The reaction solution was cooled to room temperature, 1N aqueous hydrochloric acid (3 mL) added, stirred for 30 min and diluted into ethyl acetate. The ethyl acetate solution was washed with one-half saturated aqueous sodium carbonate, water, brine, dried (Na$_2$SO$_4$) and concentrated in vacuo to afford a yellow gum, 1.2 g. Flash chromatography (3% methanol/chloroform) afforded a colorless solid, 0.82 g. $^1$H NMR (CDCl$_3$) δ 8.80 (s, 1H), 7.90 (d, 1H), 7.52 (d, 1H), 7.03 (d, 2H), 6.73 (d, 2H), 4.77 (dd, 1H), 3.98 (t, 2H, 3.58 (s, 3H), 3.08 (dd, 1H), 3.00 (t, 2H), 2.82 (t, 2H), 2.70 (dd, 1H), 2.52 (t, 2H).

Example 3d—Following the general methodology of example 1d, methyl (4-(2-(2-(6-aminopyridin-3-yl)-2(R)-hydroxyethylamino)ethoxy)phenyl)propionate was prepared from the product of Example 3c. The product was then combined with 2 equivalents of HCl gas in alcoholic solvent to afford the dihydrochloride salt. m.p. 152–155° C. $^1$H NMR (DMSO-d6) δ 9.15 (br d, 2H), 8.12 (br s, 2H), 7.89 (d, 1H), 7.88 (s, 1H), 7.10 (d, 2H), 6.99 (d, 1H), 6.85 (d, 2H), 6.38 (br s, 1H), 4.95 (dd, 1H), 4.24 (t, 2H), 3.53 (s, 3H), 3.40–3.02 (m, 4H), 2.76 (t, 2H), 2.55 (t, 2H).

Example 3e—Following the general methodology of example 1 e, (4-(2-(2-(6-aminopyridin-3-yl)-2(R)-hydroxyethylamino)ethoxy)phenyl)propionic acid was prepared. m.p. 217–218° C. $^1$H NMR (DMSO-d6) δ 7.84 (s, 1H), 7.36 (d, 1H), 7.12 (d, 2H), 6.84 (d, 2H), 6.42 (d, 2H), 6.03 (br s, 2H), 5.92 (br s, 1H), 4.80 (br s, 1H), 4.22 (t, 2H), 3.42–3.23 (m, 2H), 3.10 (t, 2H), 2.73 (t, 2H), 2.46 (t, 2H).

EXAMPLE 4

Example 4a—Following the general methodology of example 1a (4-(2-benzyloxycarbonylaminoethoxy)phenyl)acetamide was prepared from 2-(Cbz-amino)ethanol and 4-hydroxyphenylacetamide; m.p. 161–163° C.; $^1$H NMR (DMSO-d6) δ 7.45–7.37 (m, 1H), 7.30 (s, 4H), 7.10 (d, 2H), 6.79 (d, 2H), 5.00 (s, 2H), 3.91 (t,2H), 3.15 (t, 2H), 3.24 (s, 2H).

Example 4b—(4-(2-aminoethoxy)phenyl)acetamide

A slurry of 10% palladium-on-carbon (0.1 g) and (4-(2-benzyloxycarbonylaminoethoxy)phenyl)acetamide (1.00 g, 3.04 mmol) in DMF (8 mL) was treated with hydrogen (50 psi) on a Parr apparatus for 14 h. The reaction mixture was heated, filtered through Celite, washed with hot DMF (10 mL) and the combined filtrates treated with diethyl ether (75 mL) to afford a colorless solid, 320 mg; m.p. 163–165° C.; $^1$H NMR (DMSO-d6) δ 7.34 (br s, 2H), 7.10 (d, 2H), 6.80 (d, 2H), 3.84 (t, 2H), 3.23 (s, 2H), 2.81 (t, 2H).

Example 4c—The product of Example 4b is first blocked at the amino group with a trimethylsilyl group, reacted with the stereospecific oxirane, deblocked in acid, and isolated, all as described in Example 3c, thereby yielding the product, (4-(2-(2-(R)-hydroxy-2-tetrazolo[1,5-a]pyridin-6-ylethylamino)ethoxy)phenyl)acetamide.

Example 4d—The product of Example 4c is reduced as described in Example 1d to yield (4-(2-(2-(6-aminopyridin-3-yl)-2(R)-hydroxyethylamino)ethoxy)-phenyl)acetamide.

EXAMPLE 5

Example 5a—The following derivative, (4-(2-(2(R)-hydroxy-2-tetrazolo[1,5-a]pyridin-6-ylethylamino)ethoxy)phenol, was prepared utilizing the above general condition of Example 3c, from 4-(2-aminoethoxy)phenol and (2R)-(tetrazolo[1,5-a]pyrid-6-yl)oxirane. m.p. 146–149° C.; $^1$H NMR (DMSO-d6) δ 9.10 (s, 1H), 8.82 (br s, 1H), 8.11 (d, 1H), 7.84 (d, 1H), 6.69 (d, 2H), 6.60 (d, 2H), 5.76 (s, 1H), 4.82 (s, 1H), 3.87 (t, 2H), 2.90–2.66 (m, 4H).

Example 5b—Methyl (4-(2-(2(R)-hydroxy-2-tetrazolo[1,5-a]pyridin-6-ylethylamino) ethoxy)phenoxy)acetate To a cooled (5° C.), stirred solution of (4-(2-(2(R)-hydroxy-2-tetrazolo[1,5-a]pyridin-6-yl-ethylamino)ethoxy)phenol (0.90 g, 2.86 mmol) in DMF (12 mL) was added sodium hydride (60% suspension in mineral oil, 0.12 g, 3.00 mmol). The resulting mixture was maintained at 5° C. for 5 min, then allowed to stir at ambient temperature for an additional 30 min. The reaction solution was recooled to 5° C. and methyl bromoacetate (0.30 mL, 3.15 mmol) was added and the resulting dark solution was allowed to stir 2.5 h at ambient temperature. The reaction mixture was taken up in ethyl acetate, washed with water, brine, dried (Na$_2$SO$_4$) and concentrated in vacuo to afford a dark oil. Flash chromatography (2–4% methanol gradient in chloroform) afforded an off-white solid, 0.49 g. $^1$H NMR (CDCl$_3$) δ 8.85 (s, 1H), 7.93 (d, 1H), 7.56 (d, 1H), 6.83–6.75 (m, 4H), 4.80 (dd, 1H), 4.56 (s, 2H), 4.00 (t, 2H), 3.78 (s, 3H), 3.16–3.00 (m, 3H), 2.78–2.70 (dd, 1H).

Example 5c—Methyl (4-(2-(2-(6-aminopyridin-3-yl)-2(R)-hydroxyethylamino)ethoxy)phenoxy)acetate, dihydrochloride The methyl ester produced as in Example 5b was reduced as described in Example to produce the title (non-salt) compound. The product was then combined with 2 equivalents of HCl gas in alcoholic solvent to afford the dihydrochloride salt. m.p. 145–148° C. $^1$H NMR (DMSO-d6) δ 9.10 (br d, 2H), 8.10 (br s, 2H), 7.88 (d, 1H), 7.87 (s, 1H), 6.98 (d, 1H), 6.94–6.80 (m, 4H), 6.39 (br s, 1H), 4.95 (dd, 1H), 4.70 (s, 2H), 4.20 (t, 2H), 3.66 (s, 3H), 3.40–3.04 (m, 4H).

Example 5d—Following the general methodology of example 1e, (4-(2-(2-(6-aminopyridin-3-yl)-2(R)-hydroxyethylamino)ethoxy)phenoxy)acetic acid was prepared. m.p. 203–205° C. $^1$H NMR (DMSO-d6) δ 7.80 (s, 1H), 7.33 (d, 1H), 6.76 (s, 4H), 5.87 (br s, 2H), 4.67 (t, 1H), 4.38 (s, 2H), 4.05 (t, 2H), 3,15 (t, 2H), 2.94 (t, 2H).

I claim:

1. A compound having the formula

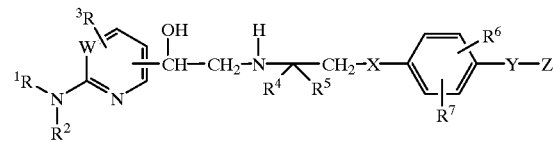

wherein:

$R^1$, $R^2$, $R^4$ and $R^5$ are independently hydrogen or ($C_1$–$C_6$) alkyl;

$R^3$, $R^6$ and $R^7$ are independently hydrogen, halogen ($C_1$–$C_6$)alkyl, nitro, cyano, trifluoromethyl, $SO_2R^8$, $SO_2NR^9R^{10}$, $NR^9R^{10}$, $COR^{11}$, $CO_2R^9$, ($C_1$–$C_6$)alkoxy, $NR^6SO_2R^8$, $NR^9COR^{11}$, $NR^9CO_2R^9$ $OR^9$, $R^8$ is independently ($C_1$–$C_6$)alkyl or ($C_1$–$C_6$)alkoxy ($C_1$–$C_6$)alkyl;

$R^9$ and $R^{10}$ are independently hydrogen, ($C_1$–$C_6$)alkyl, cycloalkyl($C_3$–$C_8$), or ($C_1$–$C_6$)alkoxy($C_1$–$C_6$)alkyl;

$R^{11}$ is independently hydrogen, ($C_1$–$C_6$)alkyl, $NR^9R^{10}$, ($C_3$–$C_8$)cycloalkyl, or ($C_1$–$C_6$)alkoxy($C_1$–$C_6$)alkyl wherein $R^9$ and $R^{10}$ are as defined above;

W is N, CH, or, when $R^3$ is bonded ω W, $CR^3$ wherein $R^3$ is defined above;

X and Y are independently a direct link, oxygen, sulfur, or $NR^1$ wherein $R^1$ is as defined above;

Z is $(CH_2)_mOR^9$, $(CH_2)_nCO_2H$, $(CH_2)_nCOR^{11}$, $(CH_2)_nSO_2NR^9R^{10}$, $(CH_2)_n$—$NR^9SO_2R^8$, $(CH_2)_nP(O)(OR^1)$ $(OR^2)$, $(CH_2)_n$—O—$(CH_2)_mCO_2H$, $(CH_2)_n$—O—$(CH_2)_mCOR^{11}$, $(CH_2)$-O-$(CH_2)_mCOR^{11}$, $(CH_2)_n$—O—$(CH_2)_mP(O)(OR^1)(OR^2)$, $(CH_2)_n$—O—$(CH_2)_mSO_2)$ $NR^9R^{10}$, or $(CH_2)_n$—O—$(CH_2)_m$—$NR^9SO_2R^8$ wherein $R^1$, $R^2$, $R^8$, $R^9$, $R^{10}$, and $R^{11}$ are defined above;

m is 1 to 6;

n is 0 to 6, provided that if Y is O or S, n is not 0;

or a pharmaceutically acceptable prodrug, provided that, when Z is $(CH_2)_nCO_2H$ or $(CH_2)_n$—O—$(CH_2)_mCO_2H$ such prodrug is not a $(C_1-C_6)$alkaly$(C_3-C_8)$cycloalkyl, or a $(C_1-C_6)$alkoxyl$(C_1-C_6)$alkyl prodrug; or a pharmaceutically acceptable salt thereof.

2. A compound as defined in claim 1, which is a free carboxylic acid.

3. A compound as defined in claim 2, wherein X is oxygen.

4. A compound as defined in claim 3, wherein W is CH.

5. A compound as defined in claim 4, wherein each of $R^1$, $R^2$, $R^3$, $R^4$, $R^5$, $R^6$ and $R^7$ are H.

6. A compound as defined in claim 5, wherein Y is oxygen or a direct link.

7. A compound as defined in claim 1, selected from the group consisting of:
(4-(2-(2-(6-Aminopyridin-3-yl)-2(R)-hydroxyethylamino)ethoxy)phenyl)acetic acid;
(4-(2-(2-(6Aminopyridin-3-yl)-2(R)-hydroxyethylamino)ethoxy)phenoxy)acetic acid;
4-(2-(2-(6-Aminopyridin-3-yl)-2(R)-hydroxyethylamino)ethoxy)benzoic acid; and
(4-(2-(2-(6-Aminopyridin-3-yl)-2(R)-hydroxyethylamino)ethoxy)phenyl)propionic acid; and the pharmaceutically acceptable salts of each of the above compounds.

8. A compound as defined in claim 7, which is (4-(2-(2-(6-Aminopyridin-3-yl)-2(R)-hydroxyethylamino)ethoxy)phenyl)acetic acid, or a pharmaceutically acceptable salt thereof.

9. A compound as defined in claim 7, which is (4-(2-(2-(6-Aminopyridin-3-yl)-2(R)-hydroxyethylamino)ethoxy)phenoxy)acetic acid, or a pharmaceutically acceptable salt thereof.

10. A compound as defined in claim 7, which is 4-(2-(2-(6-Aminopyridin-3-yl)-2(R)-hydroxyethylamino)ethoxy)benzoic acid, or a pharmaceutically acceptable salt thereof.

11. A compound as defined in claim 7, which is (4-(2-(2-(6-Aminopyridin-3-yl)-2(R)-hydroxyethylamino)ethoxy)phenyl)propionic acid, or a pharmaceutically acceptable salt thereof.

12. A pharmaceutical composition comprising an effective amount of a compound, prodrug, or salt as defined in claim 1, and a pharmaceutically acceptable carrier.

13. A method of treating a condition selected from the group consisting of diabetes, hyperglycemia and obesity in a mammal, comprising administering to a mammal in need of such treatment an amount of a compound of formula I as defined in claim 1, or a prodrug thereof, or a pharmaceutically acceptable salt of said compound or prodrug, effective in treating such condition.

14. A method of increasing the content of lean meat in edible animals comprising administering to an edible animal an amount of a compound of formula I as defined in claim 1, or a prodrug thereof, or a pharmaceutically acceptable salt of said compound or prodrug, effective in increasing said content.

15. A method for treating prostate disease in a mammal, comprising administering to a mammal in need of such treatment an amount of a compound of formula I as defined in claim 1, or a prodrug thereof, or a pharmaceutically acceptable salt of said compound or prodrug, effective in treating such disease.

16. A method of treating intestinal motility disorders, comprising administering to a mammal in need of such treatment an effective amount of a compound of formula I as defined in claim 1, or a prodrug thereof, or a pharmaceutically acceptable salt of said compound or prodrug.

17. A method of treating depression, comprising administering to a mammal in need of such treatment an effective amount of a compound of formula I as defined in claim 1, or a prodrug thereof, or a pharmaceutically acceptable salt of said compound or prodrug.

18. A method of treating dyslipidemia, comprising administering to a mammal in need of such treatment an effective amount of a compound of formula I as defined in claim 1, or a prodrug thereof, or a pharmaceutically acceptable salt of said compound or prodrug.

19. A method for treating airway inflammatory disorders, comprising administering to a mammal in need of such treatment an effective amount of a compound of formula I as defined in claim 1, or a prodrug thereof, or a pharmaceutically acceptable salt of said compound or prodrug.

20. A method as defined in claim 19, wherein said airway inflammatory disorder is asthma.

21. A compound selected from the group consisting of

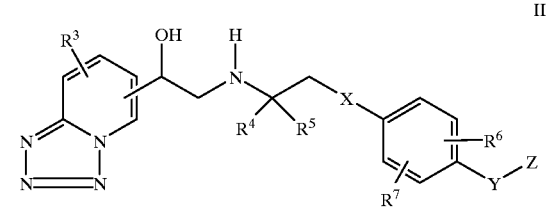

II

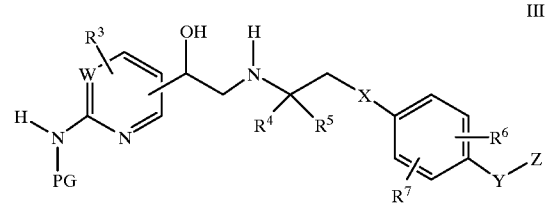

III

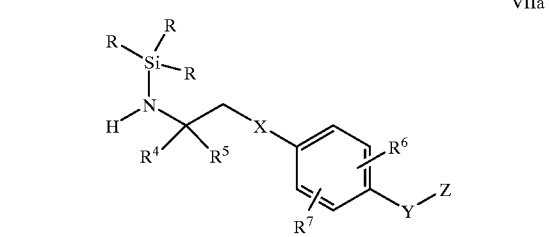

VIIa

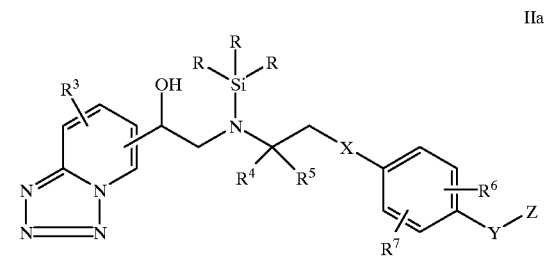

IIa and

-continued

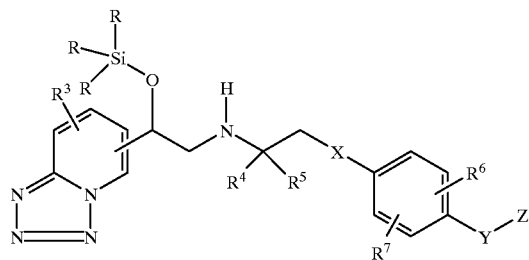

wherein:
PG is a conventional protecting group,
R is an alkyl group;
$R^1$, $R^4$ and $R^5$ are independently hydrogen or $(C_1-C_6)$ alkyl;
$R^3$, $R^6$ and $R^7$ are independently hydrogen, halogen, $(C_1-C_6)$alkyl, nitro, cyano, trifluoromethyl, $SO_2R^8$, $SO_2NR^9R^{10}$, $NR^9R^{10}$, $COR^{11}$, $CO_2R^9$, $(C_1-C_6)$alkoxy, $NR^9SO_2R^8$, $NR^9COR^{11}$, $NR^9CO_2R^9$ or $OR^9$;
$R^8$ is independently $(C_1-C_6)$alkyl or $(C_1-C_6)$alkoxy$(C_1-C_6)$alkyl;
$R^9$ and $R^{10}$ are independently hydrogen, $(C_1-C_6)$alkyl, cycloalkyl$(C_3-C_6)$, or $(C_1-C_6)$alkoxy$(C_1-C_6)$alkyl;
$R^{11}$ is independently hydrogen, $(C_1-C_6)$alkyl, $NR^9R^{10}$, $(C_3-C_8)$cycloalkyl, or $(C_1-C_6)$alkoxy$(C_1-C_6)$alkyl, wherein $R^9$ and $R^{10}$ are as defined above;
W is N, CH, or, when $R^3$ is bonded to W, $CR^3$ wherein $R^3$ is defined above;
X and Y are independently a direct link, oxygen, sulfur, or $NR^1$ wherein $R^1$ is as defined above;
Z is $(CH_2)_mOR^9$, $(CH_2)_nCOR^{11}$, $(CH_2)_nSO_2NR^9R^{10}$, $(CH_2)_n-NR^9SO_2R^8$, $(CH_2)_nP(O)(OR^1)(OR^2)$, $(CH_2)_n-O-(CH_2)_mCOR^{11}$, $(CH_2)_n-O-(CH_2)_mP(O)(OR^1)(OR^2)$, $(CH_2)_n-O-(CH_2)_mSO_2NR^9R^{10}$, or $(CH_2)_n-O-(CH_2)_m-NR^9SO_2R^8$ wherein $R^1$, $R^2$, $R^8$, $R^9$, $R^{10}$ and $R^{11}$ are as defined above;
m is 1 to 6; and
n is 0 to 6, provided that if Y is O or S, n is not 0.

* * * * *